(12) United States Patent (10) Patent No.: US 7,713,713 B2
Ohmori et al. (45) Date of Patent: May 11, 2010

(54) POLYPEPTIDE HAVING INTRACELLULAR CALCIUM ION INDICATOR FUNCTION

(75) Inventors: Harunori Ohmori, Kyoto (JP); Takahiro Ishii, Kyoto (JP); Kenji Takatsuka, Kyoto (JP)

(73) Assignee: Kyoto University, Kyoto (JP)

( * ) Notice: Subject to any disclaimer, the term of this patent is extended or adjusted under 35 U.S.C. 154(b) by 402 days.

(21) Appl. No.: 11/404,167

(22) Filed: Apr. 14, 2006

(65) Prior Publication Data

US 2007/0042345 A1 Feb. 22, 2007

(30) Foreign Application Priority Data

Aug. 18, 2005 (JP) ............................. 2005-238034

(51) Int. Cl.
*C07K 14/00* (2006.01)
*G01N 33/53* (2006.01)

(52) U.S. Cl. ........................................ 435/7.2; 530/350
(58) Field of Classification Search ....................... None
See application file for complete search history.

(56) References Cited

U.S. PATENT DOCUMENTS

2007/0298973 A1* 12/2007 Anderson et al. .............. 506/4

OTHER PUBLICATIONS

Grynkiewicz et al., *Journal of Biological Chemistry*, 260(6): 3440-3450 (Mar. 25, 1985).
Miyawaki et al., *Nature*, 388: 888-887 (Aug. 28, 1997).
Miyawaki et al., *Proc. Natl. Acad. Sci. U.S.A.*, 96: 2135-2140 (Mar. 1999).
Romoser et al., *Journal of Biological Chemistry*, 272(20): 13270-13274 (May 16, 1997).
Persechini et al., 22(3): 209-216 (1997).
Baird et al., *Proc. Natl. Acad. Sci. U.S.A.*, 96: 11241-11246 (Sep. 1999).
Griesbeck et al., *Journal of Biological Chemistry*, 276(31): 29188-29194 (Aug. 3, 2001).
Nakai et al., *Nature Biotechnology*, 19: 137-141 (Feb. 2001).
Nagai et al., *Proc. Natl. Acad. Sci. U.S.A.*, 98(6): 3197-3202 (Mar. 13, 2001).
Truong et al., *Nature Structural Biology*, 8(12): 1069-1073 (Dec. 2001).
Vanderklish et al., *Proc. Natl. Acad. Sci. U.S.A*, 97(5): 2253-2258 (Feb. 29, 2000).
Croall et al., *Physiological Reviews*, 71(3): 813-847 (Jul. 1991).
Takatsuka et al., *Biological and Biophysical Research Communications*, 336: 316-232 (2005).
Takatsuka et al., *Japanese Journal of Physiology*, 55: S204, Poster 527 (3P099) (Apr. 25, 2005) (with online version).
Takasuka et al., *The 82$^{nd}$ Annual Meeting of the Physiological Society of Japan*, presentation slides 1-10 and abstract (May 20, 2005).

* cited by examiner

*Primary Examiner*—Michael Pak
(74) *Attorney, Agent, or Firm*—Leydig, Voit & Mayer, Ltd.

(57) ABSTRACT

The present invention provides a polypeptide having an intracellular calcium ion indicator function, which contains the following elements (a)-(c):
  (a) a polypeptide residue consisting of a membrane localization signal sequence;
  (b) a first fluorescent polypeptide residue; and
  (c) a second fluorescent polypeptide residue
in the order of (a), (b) and (c) from the N-terminal side, wherein one of the two fluorescent polypeptide residues is a donor for fluorescence resonance energy transfer, the other is the corresponding acceptor, and the two fluorescent polypeptide residues are connected with a linker polypeptide residue containing at least one calpain sensitive sequence, thereby to allow fluorescence resonance energy transfer between them.

10 Claims, 9 Drawing Sheets

POLYPEPTIDE HAVING INTRACELLULAR CALCIUM ION INDICATOR FUNCTION

CROSS REFERENCE TO RELATED APPLICATION

This application is based on a patent application No. 2005-238034 filed in Japan on Aug. 18, 2005, the contents of which are hereby incorporated by reference.

TECHNICAL FIELD OF THE INVENTION

The present invention relates to a polypeptide having an intracellular calcium ion indicator function, a polynucleotide encoding the polypeptide, a vector containing the polynucleotide, a transformant containing the vector, a transgenic animal, an intracellular calcium ion indicator, a method of measuring an intracellular calcium ion concentration and the like.

BACKGROUND OF THE INVENTION

Intracellular calcium ion ($Ca^{2+}$) plays an important role in many biological phenomena such as release of neurotransmitters in synapses, activation of ion channels in cell membrane, control of cytoplasmic enzymes, contraction of muscles (skelet al. muscle, smooth muscle, cardiac muscle), activation of leukocytes, activation of platelets and the like. They are mainly induced by a transient rise of cytoplasmic $Ca^{2+}$ concentration. Therefore, an accurate measurement of intracellular $Ca^{2+}$ concentration, which is free of influence on the cell functions, is important for the understanding of many life phenomena.

The cytoplasmic concentration of free $Ca^{2+}$ has been measured by loading a chemically synthesized $Ca^{2+}$ chelator such as Fura-2 (non-patent reference 1: Grynkiewicz, G. et al., J. Biol. Chem., 260, 3440-3450, 1985). While Fura-2 is superior in sensitivity and time responsiveness to calcium ion, it has a problem in that intracellularly introduced Fura-2 gradually leaks out from the cell with the lapse of time, and the $Ca^{2+}$ sensitivity decreases with time. Since Fura-2 has a calcium ion binding activity, when the intracellular concentration of Fura-2 is raised to enhance the $Ca^{2+}$ sensitivity, the dynamics of intracellular calcium ion changes.

In recent years, many $Ca^{2+}$ probes using fluorescence resonance energy transfer (FRET) have been developed based on fluorescent protein by genetic engineering. There have been developed $Ca^{2+}$ probes using the FRET technique, such as Cameleon (non-patent reference 2: Miyawaki, A. et al., Nature, 388, 882-887, 1997/non-patent reference 3: Miyawaki, A. et al., Proc. Natl. Acad. Sci. U.S.A., 96, 2135-2140, 1999) and FIP-$CB_{SM}$ (non-patent reference 4: Romoser, V. A. et al., J. Biol. Chem., 272, 13270-13274, 1997/non-patent reference 5: Persechini, A. et al., Cell Calcium, 22, 209-216, 1997), Camgaroo (non-patent reference 6: Baird, G. S. et al., Proc. Natl. Acad. Sci. U.S.A., 96, 11241-11246, 1996/non-patent reference 7: Griesbeck, O. et al., J. Biol. Chem., 276, 29188-29194, 2001), G-CaMP (non-patent reference 8: Nakai, J. et al., Nat. Biotechnol., 19, 137-141, 2001), and Pericam (non-patent reference 9: Nagai, T. et al., Proc. Natl. Acad. Sci. U.S.A. 98, 3197-3202, 2001).

Non-patent reference 2 discloses a calcium ion indicator protein obtained by the FRET technique using a combination of fluorescent proteins ECFP and EYFP, or a combination of EBFP and EGFP. A sequence of calmodulin and myosin light chain kinase has been inserted between the two fluorescent proteins. This calmodulin sequence has a calcium ion binding site in the inside, it is highly likely that the sequence influences the movement of intracellular calcium ion, and shows physiological activities such as protein modification and the like by acting on other proteins. There have been reported proteins named YC2, YC3, YC4, split YC2 and the like. When YC2, YC3 and YC4 therefrom are expressed in Hela cells, the level of response to stimulation (emission ratio: peak value of reaction/initial value) is as small as about 1.5. Split YC2 is a mixture of proteins having a shape of YC2 protein divided into two, and shows a response level of about 1.8. The longest measurement time reported in the reference is 133 min.

Non-patent reference 3 discloses a calcium ion indicator protein free of the problem of pH sensitivity in the protein described in non-patent reference 2. The basic structure of the protein is the same as that in non-patent reference 2. Therefore, this protein, too, has a calcium ion binding site in the inside, it is highly likely that the sequence influences the movement of intracellular calcium ion, and shows physiological activities such as protein modification and the like by acting on other proteins. The level of response to stimulation (emission ratio) is not improved and is about 1.5. The longest measurement time reported in the reference is 100 min.

Non-patent reference 10 (Truong, K. et al., Nat. Struct. Biol., 8, 1069-1073, 2001) discloses a calcium ion indicator protein, having improved level of response of the protein described in non-patent reference 2. The structural modification is insertion of a sequence of a calmodulin dependent kinase between calmodulin sequences. However, this protein still has a calcium ion binding site in the inside, influences the movement of intracellular calcium ion, and highly likely shows physiological activities such as protein modification and the like by acting on other proteins. The level of response is about 2.0 when a very strong stimulation of 10 μM histamine stimulation is given. This protein is not sharp in the response to stimulation, and cannot be said to accurately reflect changes in the intracellular calcium ion concentration. The longest measurement time reported in the reference is 67 min.

Non-patent reference 5 discloses a calcium ion indicator protein obtained by FRET technique using a combination of BGFP and RGFP. This protein, too, has a calcium ion binding site in the inside, it is highly likely that the sequence influences the movement of intracellular calcium ion, and shows physiological activities such as protein modification and the like by acting on other proteins. This protein shows a very weak response to stimulation.

Non-patent reference 6 discloses a calcium ion indicator fluorescent protein having a sequence wherein the former part of the EYFP amino acid sequence has been exchanged with the latter part thereof. The former part of the fluorescent protein is connected with the latter part via a calmodulin sequence. Since this protein has a calcium ion binding site in the inside, it is highly likely that the protein influences the movement of intracellular calcium ion, and shows physiological activities such as protein modification and the like by acting on other proteins. When this protein is expressed in Hela cells, the level of response upon stimulation with 200 μM histamine is about 1.5. The longest measurement time reported in the references is 13 min.

Non-patent reference 8 discloses a calcium ion indicator protein that utilizes three-dimensional structural changes of a single fluorescent protein of GFP. In this protein, a calmodulin sequence, which is also a calcium binding site, is connected to the C-terminal of a sequence wherein the former part of the amino acid sequence of EGFP is exchanged with the latter part thereof. Therefore, it is highly likely that the protein influences the movement of intracellular calcium ion, and shows physiological activities such as protein modification and the like by acting on other proteins. When this protein is expressed in HEK-293 cells, the level of response upon stimulation with 100 µM ATP is about 1.5. The longest measurement time that reported in the references is 30 min.

Non-patent reference 9 discloses a calcium ion indicator fluorescent protein having a sequence wherein the former part of the amino acid sequence of EYFP is exchanged with the latter part. The former part of the fluorescent protein is connected with the latter part via a calmodulin sequence, which is a calcium binding site. Therefore, it is highly likely that the protein influences the movement of intracellular calcium ion, and shows physiological activities such as protein modification and the like by acting on other proteins. When this protein is expressed in Hela cells, the level of response upon stimulation with 1 µM histamine is about 2.7. The longest measurement time that reported in the reference is 83 min.

On the other hand, Vanderklish et al. reported an experiment using the FRET method for visually showing active synapses. They designed a fusion protein of ECFP and EYFP using a calpain sensitive sequence as a linker, and Shaker PDZ domain sequence at the C-terminal to target the protein to postsynaptic domain (non-patent reference 11: Vanderklish, P. W. et al., Proc. Natl. Acad. Sci. U.S.A., 97, 2253-2258, 2000). Calpain is a $Ca^{2+}$-activated protease found in extremely various mammalian cells (non-patent reference 12: Croall, D. E. et al., Physiol. Rev., 71, 813-847, 1991). This fusion protein is cleaved by calpain in a $Ca^{2+}$ sensitive manner, and permanently loses an FRET effect when the linker peptide is cleaved. Therefore, use of the fusion protein enables identification, based on the loss of an FRET effect, of the cell having or having had an increased $Ca^{2+}$ concentration due to stimulation. However, since cleavage of the linker peptide by calpain is an irreversible reaction, which makes continuous monitoring of intracellular $Ca^{2+}$ concentration change unattainable, this fusion protein cannot be used as a calcium ion indicator.

DISCLOSURE OF THE INVENTION

In view of the above-mentioned situation, the present invention aims at providing an intracellular calcium ion indicator polypeptide capable of measuring an intracellular $Ca^{2+}$ concentration, while minimizing influence on the cell function.

The present inventors first tried the FRET technique to visualize synapse activation, according to the report of Vanderklish, P. W. et al. (non-patent reference 11). To be specific, they tried identification of activated cells based on permanently changing FRET fluorescence ratio due to the $Ca^{2+}$-dependent cleavage of linker sequence by calpain. In addition, the present inventors connected, as a membrane localization signal sequence, an N-terminal palmitoylation signal of growth associated protein 43 (GAP43) (Moriyoshi, K. et al., Neuron, 16, 255-260, 1996) to the N-terminal side of a fusion protein to target the fusion protein to a cell membrane. That is, the present inventors constructed a fusion protein containing the elements of (1) membrane localization signal sequence, (2) ECFP, (3) calpain sensitive sequence, and (4) EYFP, in the order of (1), (2), (3) and (4) from the N-terminal side, expressed the fusion protein in the neurons, and measured changes in the fluorescence ratio upon stimulation of the cells.

As an unexpected result, the fusion protein was not cleaved by calpain, but rather, repeatedly showed changes of fluorescence strength ratio according to the changes in the intracellular $Ca^{2+}$ concentration. Furthermore, it has been found, by the $Ca^{2+}$ measurement and the fluorescence measurement simultaneously using Fura-2, that the fusion protein functions as a $Ca^{2+}$ indicator superior in calcium ion sensitivity and reaction rate, which resulted in the completion of the present invention shown below.

Accordingly, the present invention relates to the following.

[1] A polypeptide having an intracellular calcium ion indicator function, which comprises the following elements (a)-(c):

(a) a polypeptide residue consisting of a membrane localization signal sequence;

(b) a first fluorescent polypeptide residue; and (c) a second fluorescent polypeptide residue in the order of (a), (b) and (c) from the N-terminal side, wherein one of the aforementioned two fluorescent polypeptide residues is a donor for fluorescence resonance energy transfer, the other is the corresponding acceptor, and the aforementioned two fluorescent polypeptide residues are connected with a linker polypeptide residue containing at least one calpain sensitive sequence, thereby to allow fluorescence resonance energy transfer between them.

[2] The polypeptide of the above-mentioned [1], wherein the membrane localization signal sequence is a signal sequence capable of anchoring the polypeptide to a cell membrane via a lipid chain.

[3] The polypeptide of the above-mentioned [1], wherein the polypeptide residue consisting of the membrane localization signal sequence and the first fluorescent polypeptide residue are connected by a bond or a linker polypeptide residue consisting of 1-100 amino acids.

[4] The polypeptide of the above-mentioned [1], wherein the donor for the fluorescence resonance energy transfer is a Cyan Fluorescent Protein (CFP) residue and the corresponding acceptor is a Yellow Fluorescent Protein (YFP) residue.

[5] The polypeptide of the above-mentioned [1], wherein the calpain sensitive sequence is a µ-calpain sensitive sequence.

[6] The polypeptide of the above-mentioned [1], wherein the calpain sensitive sequence consists of a partial sequence of an amino acid sequence shown by SEQ ID NO:2, SEQ ID NO:3 or SEQ ID NO:4, which has a length of not less than 6 amino acids and calpain sensitivity.

[7] The polypeptide of the above-mentioned [1], wherein the linker polypeptide residue has a length of not more than 200 amino acids.

[8] The polypeptide of the above-mentioned [1], which consists of an amino acid sequence shown by SEQ ID NO:6, SEQ ID NO:8, SEQ ID NO:10 or SEQ ID NO:12.

[9] A polynucleotide encoding a polypeptide of any one of the above-mentioned [1]-[8].

[10] A vector comprising the polynucleotide of the above-mentioned [9].

[11] A transformant comprising the vector of the above-mentioned [10].

[12] A non-human transgenic animal capable of expressing a polypeptide of any one of the above-mentioned [1]-[8].

[13] A cell comprising a polypeptide of any one of the above-mentioned [1]-[8].

[14] An intracellular calcium ion indicator consisting of a polypeptide having an intracellular calcium ion indicator function, wherein the aforementioned polypeptide comprises the following elements (a)-(c):

(a) a polypeptide residue consisting of a membrane localization signal sequence;
(b) a first fluorescent polypeptide residue; and
(c) a second fluorescent polypeptide residue in the order of (a), (b) and (c) from the N-terminal side, wherein one of the aforementioned two fluorescent polypeptide residues is a donor for fluorescence resonance energy transfer, the other is the corresponding acceptor, and the aforementioned two fluorescent polypeptide residues are connected with a linker polypeptide residue containing at least one calpain sensitive sequence, thereby to allow fluorescence resonance energy transfer between them.

[15] A method of measuring an intracellular calcium ion concentration, which comprises the following steps of:

(A) providing a cell comprising a polypeptide having an intracellular calcium ion indicator function, wherein the polypeptide comprises the following elements (a)-(c):
(a) a polypeptide residue consisting of a membrane localization signal sequence;
(b) a first fluorescent polypeptide residue; and
(c) a second fluorescent polypeptide residue in the order of (a), (b) and (c) from the N-terminal side, wherein one of the aforementioned two fluorescent polypeptide residues is a donor for fluorescence resonance energy transfer, the other is the corresponding acceptor, and the aforementioned two fluorescent polypeptide residues are connected with a linker polypeptide residue containing at least one calpain sensitive sequence, thereby to allow fluorescence resonance energy transfer between them; and (B) irradiating an excitation light for the aforementioned donor for the fluorescence resonance energy transfer, to the cell provided in step (A), and measuring the level of the fluorescence resonance energy transfer.

EFFECTS OF THE INVENTION

Figure 1:
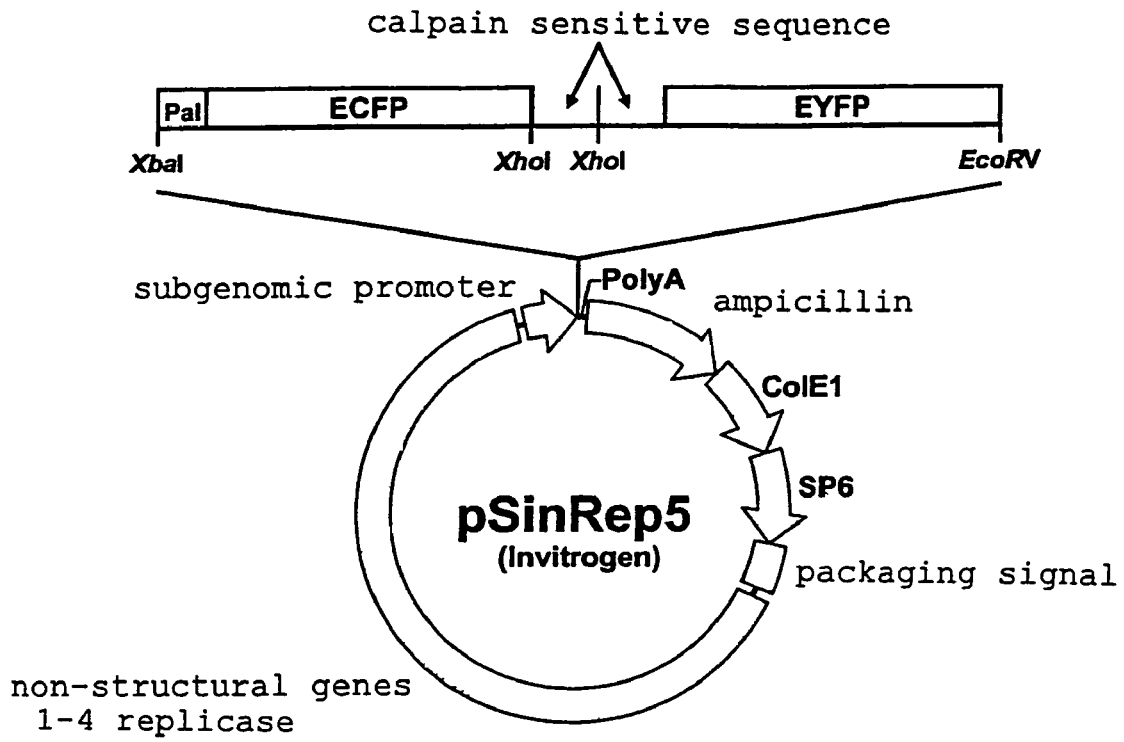
FIG. 1 is a schematic drawing showing the pSindbis-F2C construct.

With the polypeptide of the present invention, changes in the intracellular calcium ion can be measured stably with high sensitivity for a long time, while minimizing influence on the cell function. Particularly, the polypeptide of the present invention is superior in the following points, as compared to conventional intracellular calcium ion indicators.

(1) Most of the conventional calcium ion indicator proteins have a calcium ion binding site in a molecule. Therefore, when the protein is intracellularly expressed in a large amount, the movement of intracellular calcium may be markedly influenced.

In contrast, the polypeptide of the present invention does not require a calcium ion binding site in a molecule. The calcium ion indicator function of the polypeptide of the present invention is achieved by utilizing the mechanism wherein calpain, which is universally present in cells, is activated when calcium ion concentration increases, and the activated calpain recognizes the calpain sensitive site in the polypeptide of the present invention, and changes in the FRET fluorescence strength ratio occur. Since calpain, which is universally present in cells, functions as a direct calcium ion sensor, intracellular expression of a large amount an exogenous polypeptide of the present invention less likely influences the movement of the intracellular calcium ion.

(2) Most of the conventional calcium ion indicator proteins have a calmodulin sequence in a molecule as a calcium ion binding site. Since calmodulin binds to other proteins in living organism and changes the activity of the bound proteins, intracellular expression of a large amount of the protein possibly influences the cell function.

In contrast, the polypeptide of the present invention does not require a special enzymatically active site and a modification functional site in a molecule. Therefore, intracellular expression of a large amount of the polypeptide of the present invention less likely influences the cell function.

(3) The fusion protein disclosed in non-patent reference 11 is irreversibly cleaved by calpain in a $Ca^{2+}$ sensitive manner and permanently loses an FRET effect, which makes continuous monitoring of changes in the intracellular $Ca^{2+}$ concentration unattainable.

In contrast, the polypeptide of the present invention is not cleaved by calpain, and repeatedly shows changes in the fluorescence strength ratio according to the changes in the intracellular $Ca^{2+}$ concentration. Thus, continuous monitoring of changes in the intracellular $Ca^{2+}$ concentration is attainable by intracellular expression of the polypeptide of the present invention.

(4) Intracellular calcium indicators with low molecular weight such as Fura-2 and the like gradually leak out from the cell with the lapse of time, and the base line rises with time. Thus, application to the measurement of calcium ion concentration for an extended time is difficult.

In contrast, intracellular expression of the polypeptide of the present invention enables stable measurement of calcium ion response for an extended time.

(5) The polypeptide of the present invention shows high level of response (emission ratio) to changes in the calcium ion concentration.

(6) The polypeptide of the present invention is superior in calcium ion concentration sensitivity and reaction rate.

BEST MODE FOR EMBODYING THE INVENTION

1. Polypeptide

The present invention provides a polypeptide having an intracellular calcium ion indicator function, which comprises the following elements (a)-(c):

(a) a polypeptide residue consisting of a membrane localization signal sequence;

(b) a first fluorescent polypeptide residue; and (c) a second fluorescent polypeptide residue in the order of (a), (b) and (c) from the N-terminal side, wherein one of the aforementioned two fluorescent polypeptide residues is a donor for fluorescence resonance energy transfer, the other is the corresponding acceptor, and the aforementioned two fluorescent polypeptide residues are connected with a linker polypeptide residue containing at least one calpain sensitive sequence, thereby to allow fluorescence resonance energy transfer between them.

The intracellular calcium ion indicator function refers to a function capable of inducing intracellular changes in the signals (fluorescence, absorbance, luminescence etc.) depending on the calcium ion concentration. While not bound by theory, the intracellular calcium ion indicator function possessed by the polypeptide of the present invention is based on the changes in the fluorescence resonance energy transfer, which are caused by the recognition of calpain sensitive sequence in the polypeptide of the present invention by calpain activated in a calcium ion dependent manner in the cell. In other words, when the intracellular calcium ion concentration rises, the intracellular calpain is activated, the activated calpain recognizes the calpain sensitive sequence in the polypeptide of the present invention, and suppresses the fluorescence resonance energy transfer that can occur between two fluorescent polypeptide residues contained in the polypeptide of the present invention, which in turn increases the fluorescence strength of the donor and reduces the fluorescence strength of the acceptor. Conversely, when the intracellular calcium ion concentration reduces, activation of calpain is suppressed, recognition of the calpain sensitive sequence by calpain is attenuated, the suppressed fluorescence resonance energy transfer recovers, which in turn reduces the fluorescence strength of the donor and increases the fluorescence strength of the acceptor. Therefore, the polypeptide of the present invention can exert a desired calcium ion indicator function in the cell containing calpain.

The membrane localization signal sequence refers to an amino acid sequence having a function of transferring a polypeptide to the surface on the cytoplasmic side of a cell membrane (membrane localization signal function) when the polypeptide is intracellularly expressed with the amino acid sequence being connected to the N-terminal side of the polypeptide. The membrane localization signal sequence is preferably located at the N-terminal of the polypeptide of the present invention and the N-terminal amino acid thereof may be methionine derived from an initiation codon (ATG). Since a membrane localization signal sequence is present in the polypeptide of the present invention, the calpain activated in a calcium ion-dependent manner recognizes a calpain sensitive sequence in the polypeptide of the present invention without substantially cleaving the sequence and suppresses fluorescence resonance energy transfer. As a result, the polypeptide of the present invention exhibits a superior intracellular calcium ion indicator function. While not bound by theory, since the polypeptide of the present invention is transferred to the surface on the cytoplasmic side of a cell membrane due to the action of the membrane localization signal sequence, the degree of freedom in the three-dimensional structure may be limited. Consequently, it is expected that the calpain activated in a calcium ion-dependent manner recognizes a calpain sensitive sequence in the polypeptide of the present invention but cannot substantially cleave the calpain sensitive sequence due to the limitation on the three-dimensional structure and the like.

The length of the membrane localization signal sequence is not particularly limited as long as the sequence has a membrane localization signal function and the polypeptide of the present invention can exhibit the desired intracellular calcium ion indicator function. When the membrane localization signal sequence is too long, however, the degree of freedom in the three-dimensional structure of the polypeptide of the present invention may increase, which in turn may enable calpain activated in a calcium ion-dependent manner to recognize and cleave a calpain sensitive sequence in the polypeptide of the present invention without limitation on the three-dimensional structure. Consequently, fluorescence resonance energy transfer may be permanently blocked, and the polypeptide of the present invention may not be able to exhibit a desired intracellular calcium ion indicator function. In view of the above, the length is preferably as short as possible and, for example, it is about not more than 100 amino acids, preferably not more than 50 amino acids, more preferably not more than 30 amino acids.

While the kind of the membrane localization signal sequence is not particularly limited as long as the polypeptide of the present invention can exhibit a desired intracellular calcium ion indicator function, a signal sequence capable of anchoring the polypeptide to a cell membrane via a lipid chain is preferable. As such membrane localization signal sequence, aliphatic acylation signal sequence, prenylation signal sequence and the like can be mentioned. Since a prenylation signal sequence can generally function at the C-terminal of polypeptide, an aliphatic acylation signal sequence is more preferable as the membrane localization signal sequence. As the aliphatic acylation signal sequence, palmitoylation signal sequence, myristoilation signal sequence and the like can be mentioned. As the prenylation signal sequence, farnesylation signal sequence, geranylgeranylation signal sequence and the like can be mentioned.

As the membrane localization signal sequence, a sequence known per se can be used.

Examples of the palmitoylation signal sequence include, but are not limited to, N-terminal palmitoylation signal sequence (MLCCMRRTKQVEKNDEDQKI: SEQ ID NO:1) of growth-associated protin-43 (GAP43) (Moriyoshi, K. et al., Neuron, 16, 255-260, 1996). The N-terminal palmitoylation signal sequence of GAP-43 is known to function as long as 10 amino acids (MLCCMRRTKQ: SEQ ID NO:13) are present on the N-terminal side (M. X. Zuber, S. M. Strittmatter, and M. C. Fishman, A membrane-targeting signal in the amino terminus of the neuronal protein GAP-43, Nature 341 (1989) 345-348).

Many of the myristoilation signal sequences contain an amino acid sequence of $Met^1$-$Gly^2$-$X^3$-$X^4$-$X^5$-Ser/$Thr^6$, in which the number on the right shoulder shows the position from the N-terminal and X shows any amino acid (T. Utsumi, J. Kuranami, E. Tou, A. Ide, K. Akimaru, M. C. Hung, and J. Klostergaard, In vitro synthesis of an N-myristoylated fusion protein that binds to the liposomal surface, Arch. Biochem. Biophys., 326 (1996) 179-184). Examples of the myristoilation signal sequence include, but are not limited to, N-terminal myristoilation sequence of c-Src (MGSSKSKPKDPSQR: SEQ ID NO:14) (Y. Miyamoto, J. Yamauchi, N. Mizuno, and H. Itoh, The adaptor protein Nck1 mediates endothelin A receptor-regulated cell migration through the Cdc42-dependent c-Jun N-terminal kinase pathway, J. Biol. Chem., 279 (2004) 34336-34342 and W. Lu, S. Katz, R. Gupta, and B. J. Mayer, Activation of Pak by membrane localization mediated by an SH3 domain from the adaptor protein Nck, Curr. Biol., 7 (1997) 85-94) and the like.

The membrane localization signal sequence includes partial sequences of membrane localization signal sequences known per se, which have a length of not less than 6 amino acids, preferably not less than 8 amino acids, more preferably not less than 10 amino acids, as well as a membrane localization signal function. The partial sequence preferably contains an N-terminal amino acid (e.g., methionine) of a membrane localization signal sequence known per se.

In addition, the membrane localization signal sequence includes amino acid sequences having at least 70%, for example, not less than 80%, preferably not less than 85%, more preferably not less than 90%, still more preferably not less than 95%, homology with a membrane localization signal sequence known per se, as well as a membrane localization signal function.

The "homology" refers to the ratio (%) of the same or similar amino acid residues to the entire overlapped amino acid residues in an optimal alignment provided by aligning two amino acid sequences using a mathematical algorithm known in the pertinent field (preferably, the algorithm can consider introduction of a gap into one or both of the sequences for optimal alignment). The "similar amino acids" means amino acids similar in physicochemical properties and, for example, amino acids classified into the same group such as aromatic amino acid (Phe, Trp, Tyr), aliphatic amino acid (Ala, Leu, Ile, Val), polar amino acid (Gln, Asn), basic amino acid (Lys, Arg, His), acidic amino acid (Glu, Asp), amino acid having hydroxyl group (Ser, Thr), amino acid having small side chain (Gly, Ala, Ser, Thr, Met) and the like can be mentioned. It is predicted that substitution with such similar amino acids does not change phenotype of the polypeptide (or, preservative amino acid substitution). Specific examples of the preservative amino acid substitution are well known in the pertinent field, and are described in various literatures (e.g., see Bowie et al., Science, 247: 1306-1310 (1990)).

Examples of the algorithm to determine homology of amino acid sequence include, but are not limited to, the algorithm described in Karlin et al., Proc. Natl. Acad. Sci. USA, 90: 5873-5877 (1993) [this algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [this algorithm is incorporated in the GAP program in the GCG software package], the algorithm described in Myers and Miller, CABIOS, 4: 11-17 (1988) [this algorithm is incorporated in the ALIGN program (version 2.0) which is a part of the CGC sequence alignment software package], the algorithm described in Pearson et al., Proc. Natl. Acad. Sci. USA, 85: 2444-2448 (1988) [this algorithm is incorporated in the FASTA program in the GCG software package] and the like. The homology of the amino acid sequence can be appropriately calculated by the above-mentioned programs using its default parameters. For example, the homology of amino acid sequence can be calculated using a homology calculation algorithm NCBI BLAST-2 (National Center for Biotechnology Information Basic Local Alignment Search Tool) under the following conditions (matrix=BLOSUM62; gap open=11; gap extension=1; x_drop off=50; expectancy=10; filtering=ON).

In the polypeptide of the present invention, the distance between a polypeptide residue consisting of a membrane localization signal sequence and the first fluorescent polypeptide residue is not particularly limited as long as the polypeptide of the present invention can exhibit the desired intracellular calcium ion indicator function. When the distance is too long, however, the degree of freedom in the three-dimensional structure of the polypeptide of the present invention may increase, which in turn may enable calpain activated in a calcium ion-dependent manner to recognize and cleave a calpain sensitive sequence in the polypeptide of the present invention without limitation on the three-dimensional structure. Consequently, fluorescence resonance energy transfer may be permanently blocked, and the polypeptide of the present invention may not be able to exhibit a desired intracellular calcium ion indicator function. In view of the above, the distance is preferably as short as possible and, for example, the polypeptide residue consisting of the membrane localization signal sequence and the first fluorescent polypeptide residue are preferably connected with a bond or a linker polypeptide residue consisting of about 1-100 amino acids (preferably about 1-50 amino acids, more preferably about 1-25 amino acids, still more preferably about 1-10 amino acids). The amino acid sequence of the linker polypeptide residue is not particularly limited as long as the polypeptide of the present invention can exhibit the desired intracellular calcium ion indicator function.

The polypeptide of the present invention contains two fluorescent polypeptide residues, and one of them is a donor for fluorescence resonance energy transfer, and the other is the corresponding acceptor. Either of the two fluorescent polypeptide residues may be a donor. In other words, the first fluorescent polypeptide residue may be a donor and the second fluorescent polypeptide residue may be an acceptor; or the first fluorescent polypeptide residue may be an acceptor and the second fluorescent polypeptide residue may be a donor.

The fluorescence resonance energy transfer (FRET) means a phenomenon in which an optical energy (fluorescence) moves from one excited fluorescent molecule (donor) to the other fluorescence molecule (acceptor), in the state where two fluorescent molecules are approached sufficiently to each other, whereby the acceptor is excited.

The combination of the two fluorescent polypeptide residues contained in the polypeptide of the present invention is not particularly limited as long as fluorescence resonance energy transfer can occur between them. The combination of the two fluorescent polypeptide residues capable of causing fluorescence resonance energy transfer can be appropriately selected, so that the emission wavelength of the donor overlaps with the excitation wavelength of the acceptor. The combination of the donor/acceptor may be one known per se and, for example, CFP/YFP, BFP/GFP, GFP/RFP, CFP/RFP, CFP/DsRed (M. G. Erickson, D. L. Moon, and D. T. Yue, DsRed as a potential FRET partner with CFP and GFP, Biophys. J., 85 (2003) 599-611), GFP/DsRed, MiCy/mKO (S. Karasawa, T. Araki, T. Nagai, H. Mizuno, and A. Miyawaki, Cyan-emitting and orange-emitting fluorescent proteins as a donor/acceptor pair for fluorescence resonance energy transfer, Biochem. J., 381 (2004) 307-312) and the like can be used. For the name of the fluorescent polypeptide developed to date, refer to, for example, R. Y. Tsien, Building and breeding molecules to spy on cells and tumors, FEBS Lett., 579 (2005) 927-932, and the like. As used herein, CFP, YFP, BFP, GFP etc. includes respective variants (enhanced CFP (ECFP) etc., enhanced YFP (EYFP) etc., enhanced BFP (EBFP) etc., enhanced GFP (EGFP) etc., respectively). The amino acid sequences of these fluorescent polypeptides are known.

As the fluorescent polypeptide residue contained in the polypeptide of the present invention, one having at least 70%, for example, not less than 80%, preferably not less than 85%, more preferably not less than 90%, still more preferably not less than 95%, homology with the amino acid sequence of the aforementioned known fluorescent polypeptide, which can provide, when used for the present invention, fluorescence resonance energy transfer with the other fluorescent polypeptide residue contained in the polypeptide of the present invention, may be used.

The two fluorescent polypeptide residues contained in the polypeptide of the present invention are connected with a linker polypeptide residue, so that fluorescence resonance energy transfer can occur between them. The length of the linker polypeptide is not particularly limited as long as the fluorescence resonance energy transfer can occur between the aforementioned two fluorescent polypeptide residues. However, when the distance between the two fluorescent polypeptide residues is too long, energy transfer from the excited donor to the acceptor does not occur easily. As a result, the polypeptide of the present invention may not be able to exhibit the desired intracellular calcium ion indicator function. Thus, the length of the linker polypeptide residue connecting the aforementioned two fluorescent polypeptide residues is preferably as short as possible and is, for example, not more than 200 amino acids, preferably not more than 150 amino acids, more preferably not more than 100 amino acids, still more preferably not more than 80 amino acids.

The linker polypeptide residue that connects two fluorescent polypeptide residues contained in the polypeptide of the present invention contains at least one calpain sensitive sequence.

Calpain is a known cysteine protease that is activated in a calcium ion-dependent manner. Calpain is divided into two kinds of μ-calpain (calpain I) and m-calpain (calpain II) depending on the requirement for calcium ion concentration necessary for activation. It is known that the μ-calpain can be activated at a relatively low calcium ion concentration (e.g., about 3-50 μM) but activation of m-calpain requires a relatively high calcium ion concentration (e.g., about 400-800 μM). Since calpain is universally present in living organisms, the polypeptide of the present invention can exhibit a calcium ion indicator function in various kinds of cells.

A calpain sensitive sequence refers to an amino acid sequence that can be specifically recognized and cleaved by calpain. A calpain sensitive sequence can be divided into μ-calpain sensitive sequence and m-calpain sensitive sequence depending on the kind of calpain. Since the specificity of μ-calpain and that of m-calpain are similar, a certain amino acid sequence can be a μ-calpain sensitive sequence and m-calpain sensitive sequence at the same time (A. Kishimoto, K. Mikawa, K. Hashimoto, I. Yasuda, S. Tanaka, M. Tominaga, T. Kuroda, and Y. Nishizuka, Limited proteolysis of protein kinase C subspecies by calcium-dependent neutral protease (calpain), J. Biol. Chem., 264 (1989) 4088-4092). To allow the polypeptide of the present invention to exhibit a superior intracellular calcium ion indicator function at a lower calcium ion concentration, a μ-calpain sensitive sequence is preferably used as a calpain sensitive sequence. For calpain and calpain sensitive sequence, refer to D. E. Croall, and G. N. DeMartino, Calcium-activated neutral protease (calpain) system: structure, function, and regulation, Physiol. Rev., 71-(1991) 813-847 and the like.

There are a number of reports on calpain sensitive sequences based on the amino acid sequence analysis of the calpain cleavage site in the polypeptides, which are a substrate of calpain, and the like (D. E. Croall, and G. N. DeMartino, Calcium-activated neutral protease (calpain) system: structure, function, and regulation, Physiol. Rev., 71 (1991) 813-847 etc.). Any known calpain sensitive sequence can be used in the present invention as long as the polypeptide of the present invention can exhibit the desired intracellular calcium ion indicator function.

Examples of the calpain sensitive sequence include, but are not limited to, α-spectrin-derived μ-calpain sensitive sequence (GSGSGQQEVYGMMPRDGSG: SEQ ID NO:2) (P. W. Vanderklish, L. A. Krushel, B. H. Hoist, J. A. Gally, K. L. Crossin, and G. M. Edelman, Marking synaptic activity in dendritic spines with a calpain substrate exhibiting fluorescence resonance energy transfer, Proc Natl Acad Sci USA, 97 (2000) 2253-2258, A. S. Harris, D. E. Croall, and J. S. Morrow, The calmodulin-binding site in alpha-fodrin is near the calcium-dependent protease-I cleavage site, J. Biol. Chem., 263 (1988) 15754-15761), PKC α-derived μ-calpain sensitive sequence (IPEGDEEGNMELRQKFEKAKLG-PVGNKVISPSEDRKQPSNNLDRVKLT: SEQ ID NO:3) (A. Kishimoto, K. Mikawa, K. Hashimoto, I. Yasuda, S. Tanaka, M. Tominaga, T. Kuroda, and Y. Nishizuka, Limited proteolysis of protein kinase C subspecies by calcium-dependent neutral protease (calpain), J. Biol. Chem., 264 (1989) 4088-4092), PKCβ-derived μ-calpain sensitive sequence (VPPEGSEGNEELRQKFERAKIGQGTKAP-EEKTANTISKFDNNGNRDRMKLT: SEQ ID NO:4) (A. Kishimoto, K. Mikawa, K. Hashimoto, I. Yasuda, S. Tanaka, M. Tominaga, T. Kuroda, and Y. Nishizuka, Limited proteolysis of protein kinase C subspecies by calcium-dependent neutral protease (calpain), J. Biol. Chem., 264 (1989) 4088-4092) and the like.

The calpain sensitive sequence includes partial sequences of calpain sensitive sequences known per se, which have a length of, for example, not less than 6 amino acids, preferably not less than 8 amino acids, more preferably not less than 10 amino acids, still more preferably not less than 12 amino acids, as well as calpain sensitivity.

The calpain sensitive sequence includes amino acid sequences having at least 70%, for example, not less than 80%, preferably not less than 85%, more preferably not less than 90%, still more preferably not less than 95%, homology with a known calpain sensitive sequence, as well as calpain sensitivity.

Here, it is expected that the above-mentioned calpain sensitive sequence is recognized by calpain but is not substantially cleaved as long as it is present in the polypeptide of the present invention. Although not bound by theory, this may be because, as mentioned above, the polypeptide of the present invention is transferred to the surface on the cytoplasmic side of the cell membrane due to the action of a membrane localization signal sequence and the activated calpain may be subject to the limitation on the three-dimensional structure and the like. By the "polypeptide is not substantially cleaved by calpain" is meant that cleavage fragments due to calpain are not detected even when the polypeptide is treated with calpain in the presence of a sufficient concentration of calcium ion. Whether the polypeptide is substantially cleaved by calpain can be evaluated, for example, by expressing the object polypeptide in a cell containing calpain in the inside (e.g., neuron), dissolving the cell in a buffer containing a sufficient concentration of calcium ion (e.g., 10 mM HEPES-K buffer containing 20 μM $Ca^{2+}$ and 150 mM NaCl), incubating the obtained cell lysate at about 30° C. for about 30-60 min, and detecting the presence or absence of a cleavage product of the polypeptide due to calpain in the resulting reaction product by an immunological measurement method using an antibody against the polypeptide.

The number of calpain sensitive sequences contained in the linker polypeptide residue connecting the above-mentioned two fluorescent polypeptide residues is not particularly limited as long as the polypeptide of the present invention can exhibit the desired intracellular calcium ion indicator function. When the number of calpain sensitive sequences is too many, however, the length of the linker polypeptide residue eventually becomes large, and the polypeptide of the present invention may not be able to exhibit the desired intracellular calcium ion indicator function. Therefore, the number of calpain sensitive sequences contained in the aforementioned linker polypeptide residue is preferably smaller and the number may be, for example, 1-15, preferably 1-10, more preferably 1-5, still more preferably 1-3. When multiple calpain sensitive sequences are contained in the aforementioned linker polypeptide residue, the respective calpain sensitive sequences may be the same or different.

The polypeptide of the present invention may be modified. As the modification, addition of lipid chain (aliphatic acylation (palmitoylation, myristoilation etc.), prenylation (farnesylation, geranylgeranylation etc.) etc.), phosphorylation (phosphorylation of serine residue, threonine residue, or tyrosine residue etc.), acetylation, addition of sugar chain (N-glycosylation, O-glycosylation) and the like can be mentioned.

In this specification, the term "polypeptide of the present invention" is used to also mean a salt thereof. As the salt of polypeptide, salts with physiologically acceptable acid (e.g., inorganic acid, organic acid) and base (e.g., alkali met al. salt) and the like are used, with preference given to physiologically acceptable acid addition salt. As such salts, for example, salts with inorganic acid (e.g., hydrochloric acid, phosphoric acid, hydrogen bromide acid, sulfuric acid), salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like can be mentioned.

Examples of the polypeptide of the present invention include a polypeptide consisting of the amino acid sequence shown by SEQ ID NO:6, SEQ ID NO:8, SEQ ID NO:10 or SEQ ID NO:12.

The production method of the polypeptide of the present invention is not particularly limited, and the polypeptide may be produced according to a known peptide synthesis method, or using a known gene recombination technique. The peptide synthesis method may be, for example, a solid phase synthesis process or a liquid phase synthesis process. The object polypeptide can be produced by condensing a partial peptide or amino acid capable of constituting the polypeptide of the present invention with the remaining portion thereof and, when the resultant product contains a protecting group, eliminating the protecting group.

When the polypeptide of the present invention is to be produced using the gene recombination technology, a below-mentioned polynucleotide encoding the polypeptide of the present invention is first obtained, a host is transformed with an expression vector containing the polynucleotide, and the resulting transformant is cultivated to give the polypeptide. The polynucleotide and the production method of the polypeptide of the present invention using the gene recombination technology are described below in this specification.

2. Polynucleotide

The present invention provides a polynucleotide containing a nucleotide sequence encoding the above-mentioned polypeptide of the present invention. The polynucleotide may be DNA or RNA, or DNA/RNA chimera, with preference given to DNA. The polynucleotide may be a double strand or a single strand. When the polynucleotide is a double strand, it may be double stranded DNA, double stranded RNA or DNA:RNA hybrid.

As the polynucleotide of the present invention, a polynucleotide containing a nucleotide sequence shown by SEQ ID NO:5, SEQ ID NO:7, SEQ ID NO:9, or SEQ ID NO:11 can be mentioned. The nucleotide sequence shown by SEQ ID NO:5 encodes the polypeptide of the present invention consisting of the amino acid sequence shown by SEQ ID NO:6, the nucleotide sequence shown by SEQ ID NO:7 encodes the polypeptide of the present invention consisting of the amino acid sequence shown by SEQ ID NO:8, the nucleotide sequence shown by SEQ ID NO:9 encodes the polypeptide of the present invention consisting of the amino acid sequence shown by SEQ ID NO:10, and the nucleotide sequence shown by SEQ ID NO:11 encodes the polypeptide of the present invention consisting of the amino acid sequence shown by SEQ ID NO:12.

The polynucleotide of the present invention can be produced by ligating a polynucleotide encoding the aforementioned respective elements constituting the polypeptide of the present invention (polypeptide residue consisting of the membrane localization signal sequence, fluorescent polypeptide residue, linker polypeptide residue etc.) using a suitable enzyme such as ligase and the like according to a known gene recombination technology. The polynucleotide encoding the respective elements constituting the polypeptide of the present invention can be directly amplified by PCR using a suitable primer designed utilizing known sequence information of the respective elements and the sequence information described in the sequence listing in this specification and DNA clone encoding each element as a template and the like. Alternatively, the polynucleotide encoding each element may be synthesized based on the sequence information, using a polynucleotide synthesis apparatus.

The obtained polynucleotide encoding the polypeptide of the present invention can be used as it is, or after digestion with a restriction enzyme, or addition of a linker on demand, depending on the object of use. The polynucleotide may contain, on its 5' terminal side, ATG as a translation initiation codon and, on its 3' terminal side, TAA, TGA or TAG as a translation stop codon. These translation initiation codon and translation stop codon can be added using a suitable synthesized DNA adapter.

3. Vector and Transformant

The present invention provides a vector containing the above-mentioned polynucleotide of the present invention. As the vector, expression vector, cloning vector and the like can be mentioned, from which one suitable for the object can be selected. Preferable vector is an expression vector. The expression vector can be produced by functionally connecting the polynucleotide of the present invention to the downstream of a promoter in a suitable expression vector. As the kind of the vector, plasmid vector, virus vector and the like can be mentioned, from which one suitable for the host to be used can be appropriately selected.

As the host, for example, bacteria belonging to the genus *Escherichia* (*Escherichia coli* etc.), bacteria belonging to the genus *Bacillus* (*Bacillus subtilis* etc.), yeast (*Saccharomyces cerevisiae* etc.), insect cell (*Spodoptera frugiperda* cell; Sf cell etc.), insect (larva of *Bombyx mori* etc.), mammalian cells (rat neuron, simian cells (COS-7 etc.), Chinese hamster cells (CHO cells etc.) etc.) and the like can be used.

As the mammals, for example, rodents such as mouse, rat, hamster, guinea pig and the like, laboratory animals such as rabbit and the like, domestic animals such as pig, bovine, goat, horse, sheep, mink and the like, pets such as dog, cat and the like, primates such as human, monkey, rhesus monkey, marmoset, orangutan, chimpanzee and the like can be mentioned.

As the plasmid vector, *Escherichia coli*-derived plasmid vector (e.g., pBR322, pBR325, pUC12, pUC13), *Bacillus subtilis*-derived plasmid vector (e.g., pUB110, pTP5, pCl94), yeast-derived plasmid vector (e.g., pSH19, pSH15) and the like can be mentioned, from which suitable one can be appropriately selected depending on the kind of the host to be used and the object of use.

The kind of the virus vector can be appropriately selected depending on the kind of the host to be used and the object of use. For example, when the host is an insect cell, baculovirus vector and the like can be used. When the host is a mammalian cell, retrovirus vectors such as molony murine leukemia virus vector, lentivirus vector, Sindbis virus vector and the like, adenovirus vector, herpesvirus vector, adeno-associated virus vector, parvovirus vector, vaccinia virus vector, Sendai virus vector and the like can be used.

As the promoter, one capable of initiating transcription in a host can be selected depending on the kind of the host to be used. For example, when the host is bacteria belonging to the genus *Escherichia*, trp promoter, lac promoter, T7 promoter and the like are preferable. When the host is bacteria belonging to the genus *Bacillus*, SPO1 promoter, SPO2 promoter, penP promoter and the like are preferable. When the host is a yeast, PHO5 promoter, PGK promoter and the like are preferable. When the host is an insect cell, polyhedron promoter, P10 promoter and the like are preferable. When the host is a mammalian cell, subgenomic (26S) promoter, CMV promoter, SRα promoter and the like are preferable.

The vector of the present invention may contain an enhancer, a splicing signal, a poly A addition signal, a selection marker, SV40 replication origin (hereinafter sometimes to be abbreviated as SV40 ori) and the like, each in a functional form. As the selection marker, for example, dihydrofolate reductase (hereinafter sometimes to be abbreviated as dhfr) gene [methotrexate (MTX) resistant], ampicillin resistant gene (sometimes to be abbreviated as $Amp^r$), neomycin resistant gene (sometimes to be abbreviated as $Neo^r$, G418 resistant) and the like can be mentioned.

By introducing the above-mentioned vector of the present invention into the above-mentioned host according to a gene transfer method known per se (e.g., lipofection method, calcium phosphate method, microinjection method, proplast fusion method, electroporation method, DEAE dextran method, gene transfer method using gene gun etc.), a transformant containing the vector (transformant of the present invention) can be produced. Using an expression vector as a vector to be introduced, the transformant can express the polypeptide of the present invention. The transformant of the present invention is useful for the production of the polypeptide of the present invention, measurement of intracellular calcium ion concentration and the like.

The polypeptide of the present invention can be produced by culturing the transformant of the present invention by a method known per se according to the kind of the host, and isolating the polypeptide of the present invention from the culture. A transformant of a bacterial host belonging to the genus *Escherichia* is cultured in an appropriate medium such as LB medium, M9 medium and the like, generally at about 15-43° C. for about 3-24 hr. A transformant of a bacterial host belonging to the genus *Bacillus* is cultured in an appropriate medium, generally at about 30-40° C. for about 6-24 hr. A transformant of a yeast host is cultured in an appropriate medium such as Burkholder medium and the like, generally at about 20° C.-35° C. for about 24-72 hr. A transformant of a insect cell host or insect host is cultured in an appropriate medium such as Grace's Insect medium supplemented with about 10% bovine serum and the like, generally at about 27° C. for about 3-5 days. A transformant of an animal cell host is cultured in an appropriate medium such as MEM medium supplemented with about 10% bovine serum and the like, generally at about 30° C.-40° C. for about 15-60 hr. In any culture, aeration and stirring may be performed as necessary. The polypeptide of the present invention can be isolated or purified from the culture by, for example, subjecting the cell lysate or culture supernatant to multiple chromatographys such as reversed-phase chromatography, ion exchange chromatography, affinity chromatography and the like.

Using the transformant of the present invention, intracellular calcium ion concentration can be measured according to the method described later in this specification. When an intracellular calcium ion concentration is measured using the transformant of the present invention, the host is preferably a mammalian cell. This is because calpain is universally expressed in mammalian cells, and therefore, the polypeptide of the present invention can exhibit the desired intracellular calcium ion indicator function.

4. Transgenic Animal

The present invention provides a non-human transgenic animal capable of expressing the above-mentioned polypeptide of the present invention. Use of the transgenic animal of the present invention enables measurement of the intracellular calcium ion concentrations in various tissue-derived cells. Use of the transgenic animal enables in vivo measurement of the intracellular calcium ion concentration. The transgenic animal may be the aforementioned mammal.

The transgenic animal of the present invention can be produced by introducing the above-mentioned polynucleotide of the present invention into an animal. In this case, the polynucleotide can be functionally connected to the downstream of a suitable promoter, and used in the form of an expression vector.

The promoter is not particularly limited as long as it can initiate intracellular transcription in the animal into which the polynucleotide of the present invention is introduced and, for example, a promoter applicable to the aforementioned mammalian cell host can be mentioned. The expression vector is not particularly limited as long as it can introduce the polynucleotide of the present invention into the cell of the object animal and, for example, vectors (plasmid vector, virus vector) usable for the production of the aforementioned transformant (transformant being a mammalian cell) can be mentioned. As the virus vector, the aforementioned virus vectors applicable to mammalian host cells can be mentioned.

As a method for introducing the polynucleotide of the present invention into an animal, for example, a method for injecting the above-mentioned expression vector directly into an animal can be used. In this case, a sufficient amount of an expression vector is injected into an animal, so that the vector will be certainly delivered to the target cells in the object non-human animal. From the aspects of introduction efficiency and the like, the expression vector is preferably a virus vector. When a plasmid vector is used as the expression vector, it is desirably injected into an animal together with an appropriate transfection reagent.

For example, as described in the below-mentioned Examples, a Sindbis virus vector containing the polynucleotide of the present invention is intracerebrally injected into a non-human animal to produce a non-human transgenic animal where the polynucleotide of the present invention has been introduced into the cerebral neuron. Whether the non-human transgenic animal, into which the polynucleotide of the present invention has been introduced, can express the polypeptide of the present invention can be determined with the fluorescence of the polypeptide of the present invention as an index.

However, the aforementioned direct injection of an expression vector into an animal often results in defective transmission to progeny, since the introduced polynucleotide of the present invention fails to enter the germ line. Therefore, for more ensured introduction of the polynucleotide of the present invention into the germ line, the above-mentioned expression vector can be introduced into a fertilized egg of a non-human animal, an embryonic stem cell (hereinafter to be abbreviated as ES cells) etc., and from individuals developed using these cells, an individual is selected, in which the polynucleotide of the present invention has been incorporated into the chromosome in any cells including the germ line cells. In this way, a non-human transgenic animal can be produced, where the polynucleotide of the present invention is stably incorporated into the chromosome, and the polypeptide of the present invention can be expressed stably. The presence of the polynucleotide of the present invention introduced into the germ line cells in the produced non-human transgenic animal can be confirmed with an index that the offsprings of the produced animal have the polynucleotide of the present invention introduced into every germ line cell and somatic cell. Selection of individual is performed by confirming, at a DNA level, the presence of the polynucleotide of the present invention introduced into chromosomal DNA prepared from a tissue constituting the individual (e.g., blood tissue, a part of tail and the like). The individual thus selected is generally a heterozygote having the polynucleotide of the present invention introduced into one of the homologous chromosomes, and therefore, a homozygous animal having the introduced polynucleotide in both homologous chromosomes can be obtained from the offsprings by mating heterozygous individuals. By mating within homozygous individuals, all offsprings become homozygotes that stably retain the polynucleotide. Accordingly, propagation passage of the non-human transgenic animal of the present invention can be performed in a normal breeding environment.

For example, a non-human transgenic animal having a chromosomal DNA containing the introduced polynucleotide of the present invention can be obtained by introducing an expression vector containing the polynucleotide of the present invention into a fertilized egg by the microinjection method, a method using a retrovirus and the like, and transplanting and implanting the fertilized egg artificially in a non-human female animal.

In addition, a non-human chimeric animal partially containing cells having a chromosomal DNA containing the introduced polynucleotide of the present invention can be obtained by introducing the polynucleotide of the present invention into ES cells of the non-human animal, introducing the obtained ES cells into a fertilized egg of the non-human animal by an aggregation chimera method or an injection chimera method, and artificially transplanting and implanting the obtained chimeric embryo into a female non-human mammal.

For introduction of the polynucleotide of the present invention into ES cells, an expression vector containing the polynucleotide is introduced into ES cells by a known transfection method (e.g., calcium phosphate method, electric pulse method, lipofection method, agglutination method, microinjection method, particle gun method, DEAE-dextran method, virus vector method etc.). While the expression vector can be used in any of a cyclic form and a linearized form, it is preferable to linearize and introduce the vector without destroying the region encoding the polypeptide of the present invention and the expression regulatory region such as promoter and the like.

Furthermore, a non-human transgenic animal having a chromosomal DNA containing the introduced polynucleotide of the present invention can be obtained by mating a non-human chimeric animal with a normal animal or mating within chimeric animals, and selecting an individual having the introduced polynucleotide of the present invention from the next generation (F1) individuals. An animal (except human) having the polynucleotide of the present invention can be selected in the same manner as above by confirming, at a DNA level, of the presence of the polynucleotide of the present invention introduced into chromosomal DNA prepared from a tissue constituting an individual (e.g., blood tissue, a part of tail and the like).

5. Cell Containing Polypeptide of the Present Invention

In addition, the present invention provides a cell comprising the above-mentioned polypeptide of the present invention. Since the polypeptide of the present invention has a superior intracellular calcium ion indicator function, a cell comprising the polypeptide is useful for the measurement of an intracellular calcium ion concentration. The cell of the present inventions is preferably a mammalian cell. This is because the polypeptide of the present invention can exhibit the desired intracellular calcium ion indicator function, since calpain is universally expressed in the mammalian cells. As the mammal, the aforementioned examples can be mentioned. While the kind of the cell is not particularly limited, the cell of the present inventions may be a calpain expressing cell, so that the polypeptide of the present invention can exhibit the desired intracellular calcium ion indicator function. Examples of the calpain expressing cell include, but are not limited to, neuron, muscle cell and the like. Generally, mammalian cell is a calpain expressing cell.

As the cell containing the polypeptide of the present invention, for example, the following can be mentioned:

(1) a transformant comprising an expression vector containing the polynucleotide of the present invention functionally connected to the downstream of a promoter;

(2) a cell derived from a non-human transgenic animal, which is capable of expressing the polypeptide of the present invention;

(3) a cell comprising the polypeptide of the present invention.

The transformant of (1) can be produced in the same manner as above. The transformant can contain an expressed polypeptide of the present invention.

The cell derived from the transgenic animal of (2) can be obtained by isolating the cell from the non-human transgenic animal of the present invention, which is produced in the same manner as above. The cell can be isolated from an animal by a method known per se. For example, the cell can be isolated by removing a tissue from the animal, and treating the tissue with an enzyme such as collagenase, trypsin, DNase and the like. The cell can contain an expressed polypeptide of the present invention.

The cell of (3) can be produced by introducing the polypeptide of the present invention into a cell. The polypeptide can be introduced into a cell using a reagent for polypeptide introduction. As the polypeptide introduction reagent, Profect (manufactured by Nacalai Tesque), ProVectin (manufactured by IMGENEX) and the like can be used.

6. Intracellular Calcium Ion Indicator and Method of Measuring Intracellular Calcium Ion Concentration As mentioned above, since the polypeptide of the present invention has a superior intracellular calcium ion indicator function, it is useful as an intracellular calcium ion indicator, and the intracellular calcium ion concentration can be measured using the polypeptide.

In this specification, the "measurement of intracellular calcium ion concentration" means measurement of time-course changes, spatial distribution and the like of the absolute or relative value of the intracellular calcium ion concentration.

When the intracellular calcium ion concentration is to be measured using the polypeptide of the present invention, a cell comprising the polypeptide of the present invention is first provided. The cell can be the aforementioned cell of the present invention. The cell can contain the polypeptide of the present invention in an amount sufficient to enable measurement of the intracellular calcium ion concentration.

For example, a cell comprising the polypeptide of the present invention can be obtained by introducing, into the desired cell to be the subject of measurement, an expression vector containing the polynucleotide of the present invention functionally connected to the downstream of a promoter, and expressing the polypeptide of the present invention in the cell. Furthermore, a cell comprising the polypeptide of the present invention can also be obtained by isolating the desired cell to be the subject of measurement from a non-human transgenic animal capable of expressing the polypeptide of the present invention. Alternatively, the polypeptide of the present invention may be introduced into the desired cell to be the subject of measurement, using a reagent for polypeptide introduction.

Then, an excitation light for the donor, from the two fluorescent polypeptide residues contained in the polypeptide of the present invention, is irradiated to the provided cells and the level of the fluorescence resonance energy transfer is measured. The level of the fluorescence resonance energy transfer is evaluated by measuring the fluorescence strength at the emission wavelength of the donor (donor fluorescence) and the fluorescence strength at the emission wavelength of the acceptor (acceptor fluorescence), both of the cells to which the excitation light was irradiated, using a fluorescence spectrophotometer, a flow cytometer, a fluorescence microscope and the like, and determining the ratio of the two (donor fluorescence/acceptor fluorescence etc.), and the like. Using the fluorescence ratio, intracellular calcium ion concentration can be measured without influence of optical thickness such as cell thickness and the like. When a calcium ion is absent, the donor fluorescence is attenuated and the acceptor fluorescence is enhanced by the fluorescence resonance energy transfer, and therefore, the (donor fluorescence/acceptor fluorescence) ratio is expected to decrease relatively. When the calcium ion concentration rises, the activated calpain recognizes a calpain sensitive sequence, the fluorescence resonance energy transfer is suppressed, the donor fluorescence is enhanced, the acceptor fluorescence is attenuated, and the (donor fluorescence/acceptor fluorescence) ratio is expected to have relatively risen.

Moreover, it is possible to draw a calibration curve by measuring, in advance, the (donor fluorescence/acceptor fluorescence) ratio when a known concentration of calcium ion is flown into the above-mentioned cells using a calcium ionophore (ionomycin, A23187 etc.) in a buffer having the known calcium ion concentration, and plotting the calcium ion concentration and the (donor fluorescence/acceptor fluorescence) ratio. Therefore, it is possible to determine the absolute value of the calcium ion concentration by comparing the (donor fluorescence/acceptor fluorescence) ratio of a sample having an unknown calcium ion concentration with the calibration curve.

The present invention is explained in more detail in the following by referring to Examples, which are not to be construed as limitative.

EXAMPLES

Example 1

1. Material and Method (Primary Culture of Cerebella Purkinje Cells)

Purkinje cells were cultured in the same manner as reported previously (Weber, A. et al., Brain Res., 311, 119-130, 1984/Hirano, T. et al., Proc. Natl. Acad. Sci. U.S.A., 83, 1945-1949, 1986). In short, cerebella were dissected from Wistar rat fetus (about 20 days of fetal stage), and meninges were removed. The cerebella were incubated at 20° C. for 4 min in 1% trypsin (Invitrogen, California, U.S.A.)/0.05% DNase (Sigma, Missouri, U.S.A.) solution containing 137 mM NaCl, 5 mM KCl, 7 mM $Na_2PO_4$, and 25 mM HEPES (pH 7.2). After washing with $Ca^{2+}$- and $Mg^{2+}$-free Hanks' balanced salt solution (Invitrogen) three times, the tissue was dispersed by trituration with a fire polished Pasteur pipette in $Ca^{2+}$-free Hanks' balanced salt solution containing 0.05% DNase and 12 mM $MgSO_4$. The cell suspension was centrifuged at 180×g at room temperature and the pelletized cells were resuspended at a concentration of $10^6$ cells per 1 ml in a defined medium, which facilitates the survival of neurons (Weber, A. et al., Brain Res., 311, 119-130, 1984/Fischer, G. et al., Neurosci Lett, 28, 325-329, 1982). 2 ml of this cell suspension was plated on a Petri dish containing several heat-sterilized glass coverslips coated with 0.01% poly-L-lysin (Sigma). This cell culture was incubated at 37° C. in 5% $CO_2$. The cells on the glass coverslips were used for infection with Sindbis virus. Purkinje cells showed action potentials and robust synaptic responses during the culture for at least 9 weeks.

(In Vivo Injection of Sindbis-F2C and Preparation of Slice)

Young Wistar rats (9-10 days old) were anesthetized with chloral hydrate (0.3 mg/g body weight). Then, the head of rat was fixed on a stereotaxis stage with a pair of ear bars and a nose clamp (SR-5N, Narishige, Tokyo, Japan). The head skin was sagittally incised and a small hole was made through the skull to expose the cerebellum. A micropipette was inserted through cerebellum, and a suspension of Sindbis virus encoding F2C protein (Sindbis-F2C) was injected (0.5-1 μl) into the brainstem by applying a mild positive pressure to the micropipette with the mouth. The incised part of the skin was then sutured and the rat was returned to the mother after recovery from anesthesia.

Two days after the injection, coronal slices (200-300 μm) of brainstem having an approximate height of cochlear nuclei were prepared. The rats were deeply anesthetized with diethyl ether, decapitated, and the brainstem was quickly separated. The block of brainstem was cooled in an ice-cooled 35 mM glucose saline (35GS: 130 mM NaCl, 4.5 mM KCl, 2 mM $CaCl_2$, 5 mM PIPES-Na and 35 mM glucose, pH 7.4) saturated with 100% $O_2$ and then imbedded in a 4% agarose gel (Low gelling temperature, Nacalai Tesque, Kyoto, Japan) prepared with the 35GS. Brain slices were made with a tissue slicer (Pro-1, Dosaka, Kyoto, Japan) in the ice-cooled 35GS. The slices were preincubated in an oxygenated high-glucose artificial cerebrospinal fluid (HG-ACSF) at 37° C. for at least 1 hr before conducting the imaging experiments. HG-ACSF contained 75 mM NaCl, 2.5 mM KCl, 26 mM $NaHCO_3$, 1.25 mM $NaH_2PO_4$, 2 mM $CaCl_2$, 1 mM $MgCl_2$ and 100 mM glucose.

(Gene Construction)

An intracellular calcium ion indicator protein (named F2C, FIG. 1) was designed as a fusion protein of N-terminal icosapeptide (palmitoylation signal) of GAP43 (palmitoylation signal sequence was provided by Dr. Kaneko, Graduate School of Medicine, Kyoto University), enhanced CFP, a calpain sensitive sequence of α-spectrin, and enhanced YFP. The calpain sensitive sequence of α-spectrin was the following amino acid sequence: GSGSGQQEVYGMMPRDGSG (SEQ ID NO:2), which was the same as that reported by Vanderlklish et al. (Vanderklish, P. W. et al., Proc. Natl. Acad. Sci. U.S.A., 97, 2253-2258, 2000). The cDNAs of ECFP and EYFP were amplified by the polymerase chain reaction (PCR) from pECFP-N1 (Clontech, California, U.S.A.) and pEYFP-C1 (Clontech), respectively, as templates. F2C has two identical calpain sensitive sequences of α-spectrin (FIG. 1) in a linker connecting ECFP and EYFP. This construct was digested with XbaI and EcoRV and ligated into the pSinRep5 multiple cloning site (pSindbis-F2C).

The amino acid sequence of F2C is shown in SEQ ID NO:6 and the polynucleotide sequence is shown in SEQ ID NO:5. In the amino acid sequence shown by SEQ ID NO:6, amino acid position 1-20 corresponds to the palmitoylation signal sequence, amino acid position 21-26 corresponds to the linker polypeptide residue connecting the palmitoylation signal sequence and ECFP, amino acid position 27-265 corresponds to the ECFP residue, amino acid position 266-307 corresponds to the linker polypeptide residue connecting the ECFP residue and the EYFP residue, and amino acid position 308-546 corresponds to the EYFP residue.

(Virus Production)

Sindbis virus (Sindbis-F2C) encoding F2C protein was produced according to the instructions of the Sindbis Expression System (Invitrogen), as shown below. A capped transcription product of recombinant RNA was synthesized from the pSindbis-F2C containing the construct of F2C. Sindbis viral particles were obtained by co-infecting baby hamster kidney (BHK) cells electrophoretically with the capped recombinant RNA transcription product, and DH (26S) 5'SIN helper RNA encoding the structural protein. The virus particles in the culture supernatant were concentrated by centrifugation (6,000×g, 16 hr, 4° C.). The virus was stored in aliquots at −80° C. until use. The resulting Sindbis virus was replication-deficient and unlikely to produce the parent virus in the infected cells (Bredenbeek, P. J. et al., J. Virol., 67, 6439-6446, 1993). Cultured cells and slices were transiently infected with Sindbis-F2C and the experiments were performed 24-48 hr later.

(SDS-PAGE, Western Blot Hybridization)

To obtain cell lysate, cells were pelletized and homogenized in EGTA buffer (10 mM EGTA-Na, 10 mM HEPES-K, 150 mM NaCl) or Ca-EGTA buffer (10 mM $CaCl_2$, 10 mM EGTA-Na, 10 mM HEPES-K, 150 mM NaCl). The $Ca^{2+}$ concentration was finally adjusted to 20 μM. The cell lysates contained the protease inhibitor cocktail (Nacalai Tesque). The cell lysates were incubated at 30° C. for 30 min or 60 min. In some experiments, cell lysates were incubated with a purified μ-calpain (Calpain I, Calbiochem, California, U.S.A.) at 30° C. for 30 min or 60 min. These cell lysates were centrifuged at 20,000×g for 20 min and the supernatants were fractionated. The supernatants were loaded onto 10% SDS-PAGE gels. Western blotting was carried out according to the method of Towbin et al. (Towbin, H. et al., Proc. Natl. Acad. Sci. U.S.A., 76, 4350-4354, 1979), using mouse anti-GFP antibody for detecting F2C cleavage (dilution rate 1:1000, MBL, Nagoya, Japan) and anti-PKC α antibody (dilution rate 1:500, Upstate, N.Y., U.S.A.) to confirm calpain activity.

(Image Analysis)

The primary culture of cerebellum was incubated at 37° C., in 5% $CO_2$ and 95% $O_2$ atmosphere. The cells on a cover glass slip were infected with Sindbis-F2C 24 hrs before the incubation with Fura-2/AM (Molecular Probes, Eugene, Oregon, U.S.A.). This glass slip was transferred to a new dish filled with an external solution (ACSF, artificial cerebro-spinal fluid; 155 mM NaCl, 2.5 mM $CaCl_2$, 1 mM $MgCl_2$, 10 mM, HEPES, 17 mM glucose and 5 mM KOH and adjusted to pH 7.4). Fura-2/AM was added to a final concentration of 20 μM, and further incubated for 30 min at 37° C. Fura-2/AM (10 mM) stock was dissolved in DMSO. Cerebella cultures were transferred under the upright microscope equipped with a cooled CCD camera, and the image was prepared (ORCA-ER on Aquacosmos, Hamamatsu Photonics, Hamamatsu, Japan). For Fura-2 imaging, excitation light at wavelength 340 nm (10 nm band widths, 100% transmission) and excitation light at wavelength 380 nm (10 nm band widths, 100% transmission) were alternately applied, and fluorescence was captured at 510 nm and at longer wavelength. When F2C fluorescence was measured simultaneously, excitation light at 440 nm (10 nm band widths, 100% transmission) was applied and the fluorescence at a wavelength longer than 510 nm was captured. This fluorescence corresponds to EYFP. When FRET was measured from brain slice preparations or from cerebella cultures, neurons were excited at 440 nm (20 nm band width 60% transmission, XF1071 Omega Optical) with a dichroic mirror at 435 ram (XF2034 Omega Optical) and the fluorescence was monitored through 480 nm (30 nm bandwidth 75% transmission, XF3075 Omega Optical) for ECFP and 535 nm (25 nm bandwidth 70% transmission, XF3079 Omega Optical+50% ND filter) for EYFP.

(Calpain Inhibitor)

To test the inhibition of calpain activities, calpain inhibitor-1 (ALLN, Calbiochem) and calpain inhibitor-2 (ALLM, Calbiochem) were adopted and Fura-2 fluorescence and EYFP fluorescence measurements were similarly conducted. The primary cultures of cerebellum were preincubated in ACSF containing ALLN (100 μM in DMSO), ALLM (50 μM in DMSO) or a combination of both for 1 hr. The same concentration of DMSO was added to ACSF as a control.

2. Results (Expression of F2C Protein and Western Blotting Analysis)

Figure 2:
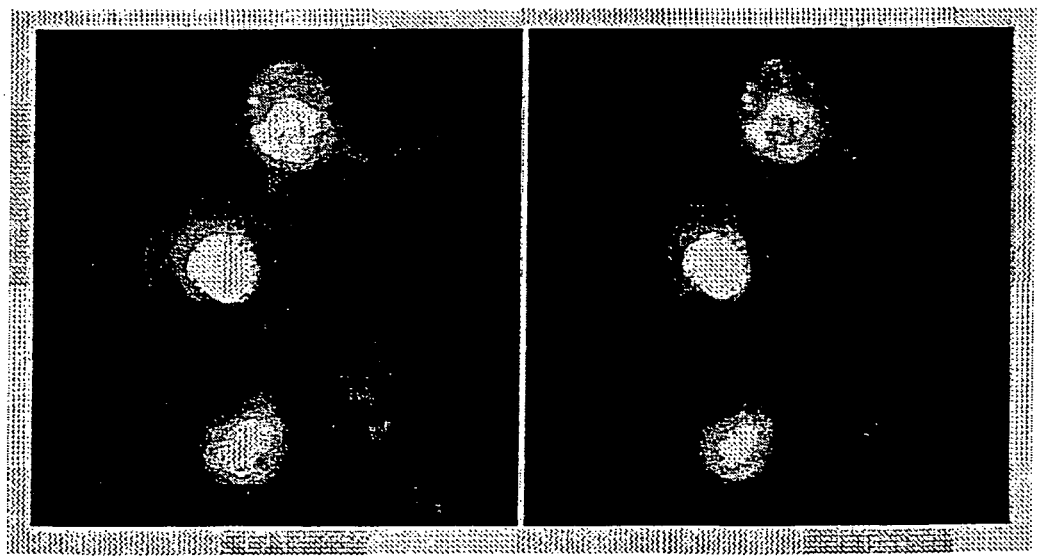
FIG. 2 is a photograph showing a fluorescence image of Purkinje cells expressing F2C, wherein the left is 480 nm emission, and the right is 535 nm emission under the conditions of excitation through 440 nm and dichroic mirror at 455 nm.

When F2C was expressed in a primary culture of rat cerebellum, Purkinje cells infected with Sindbis-F2C showed bright fluorescence (FIG. 2) in the cell body than in the dendrite. FIG. 2A and FIG. 2B show fluorescence of ECFP and EYFP, respectively. The fusion protein would have been associated with cell membranes by palmitoylation signal, but was highly located in the cell nuclei. This could indicate that fusion protein was rapidly translated in the nuclei and aggregated fluorescence was shown (Furuta, T. et al., J. Histochem. Cytochem., 49, 1497-1508, 2001).

Figure 3:
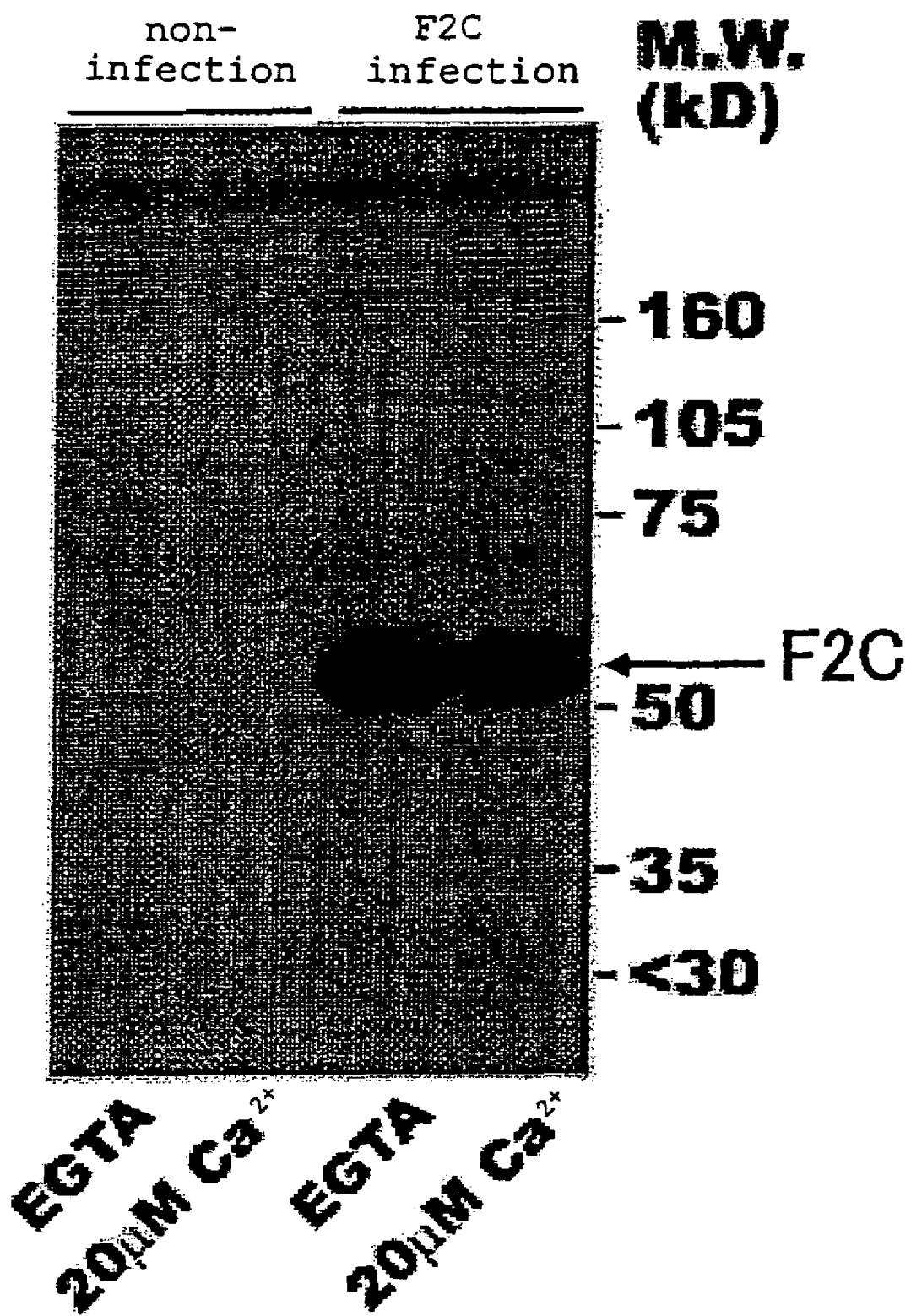
FIG. 3 shows the results of Western blotting of F2C.
Figure 4:
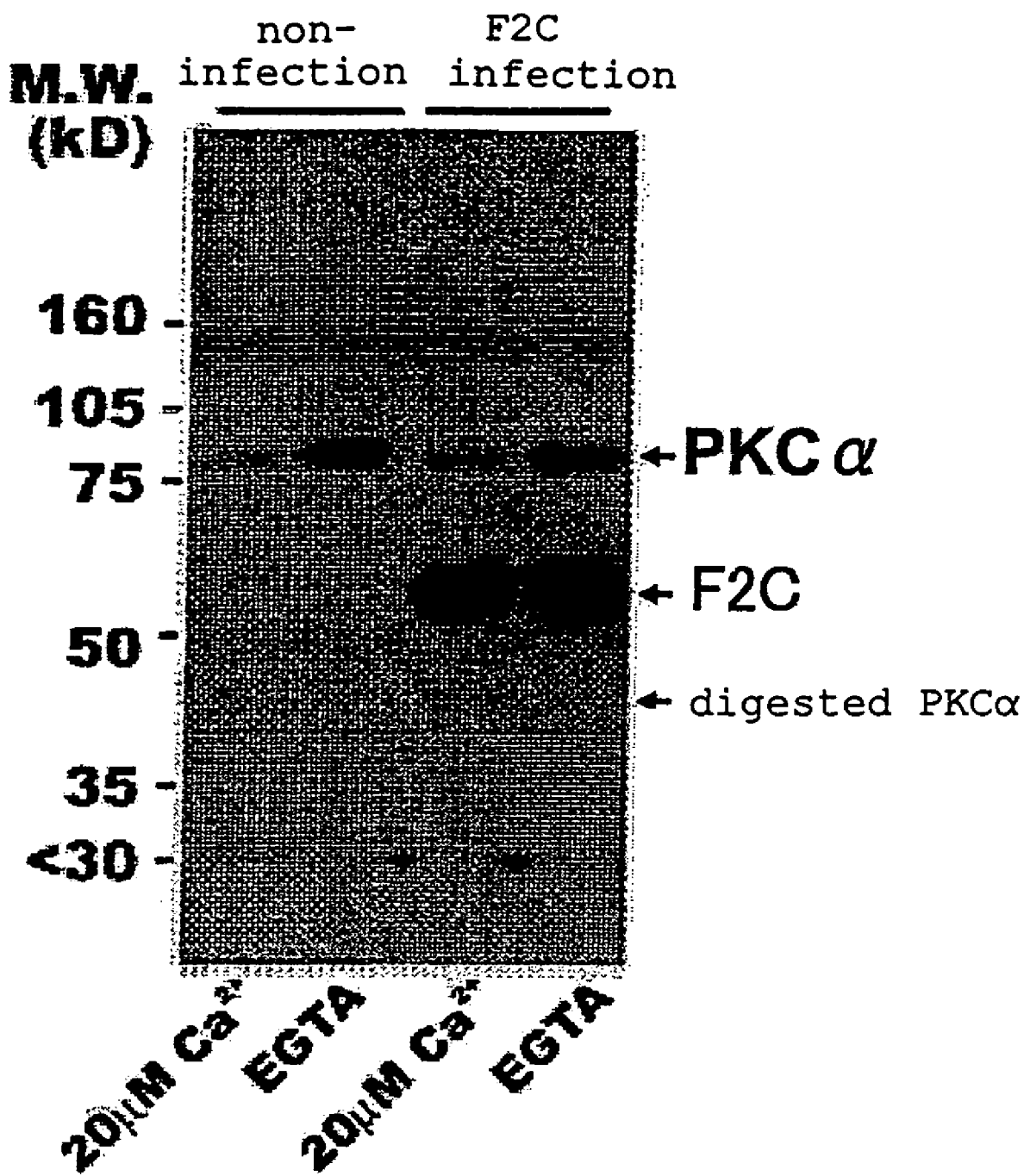
FIG. 4 shows the results of Western blotting of F2C and PCKα.

SDS-PAGE and Western blotting analyses revealed that this construct gave rise to a 61.2 kDa fusion protein. Anti-GFP antibody recognized ECFP and/or EYFP and the signal thereof was detected when primary cultures were infected with Sindbis-F2C and was not detected when primary cultures were not infected (FIG. 3). The μ-calpain requires micromolar level calcium for its activation. When the cell lysate was homogenized in Ca-EGTA buffer ($Ca^{2+}$ concentration of Ca-EGTA buffer was 20 μM), fragmented F2C was not detected (FIG. 3), while fragmented PKC-α was detected by anti-PKC-α antibody as a control of digestion by calpain (FIG. 4). Furthermore, F2C was incubated with the purified μ-calpain (Calbiochem) in Ca-EGTA buffer. However, fragmented F2C signal was not detected (data not shown).

These experiments indicate that F2C fusion protein was not cleaved by calpain.

(Application of F2C In Vitro and In Vivo)

Figure 5A:
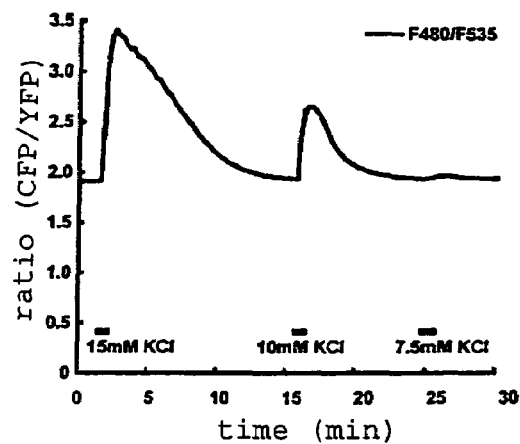
FIG. 5 shows the results of the measurement of FRET fluorescence ratios in Purkinje cells in the culture and auditory neurons in brain slices. The time course of fluorescence intensities was measured in Purkinje cells (A, B) and in cochlear nucleus cells (C, D) expressing F2C. Small black bars on abscissa indicate the timing of application of KCl to the external solution. A and C shows changes in the FRET fluorescence ratio (ECFP/EYFP). B and D show reciprocal changes of fluorescence from ECFP (F480 nm) and EYFP (F535 nm). The fluorescence intensities of F480 and F535 were plotted after normalization by the initial fluorescence intensity $F_0$ (B, D). $F_0$ was defined as the average intensity of the first 5 measurements.
Figure 5B:
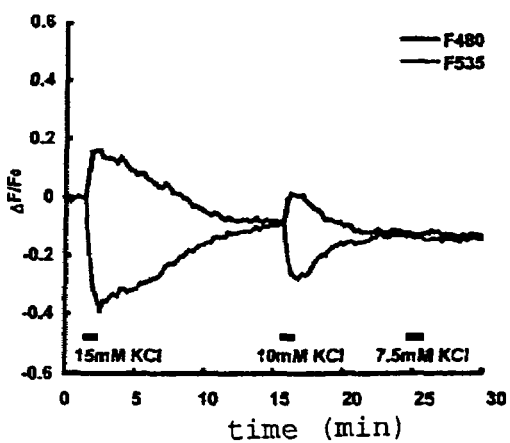
Figure 5C:
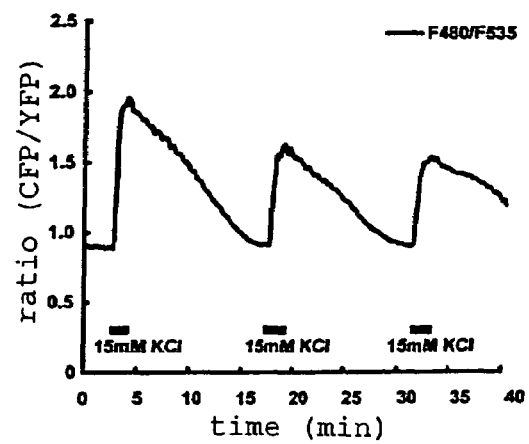
Figure 5D:
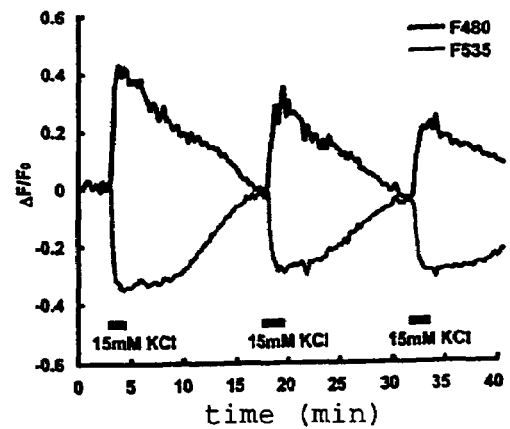
Figure 9:
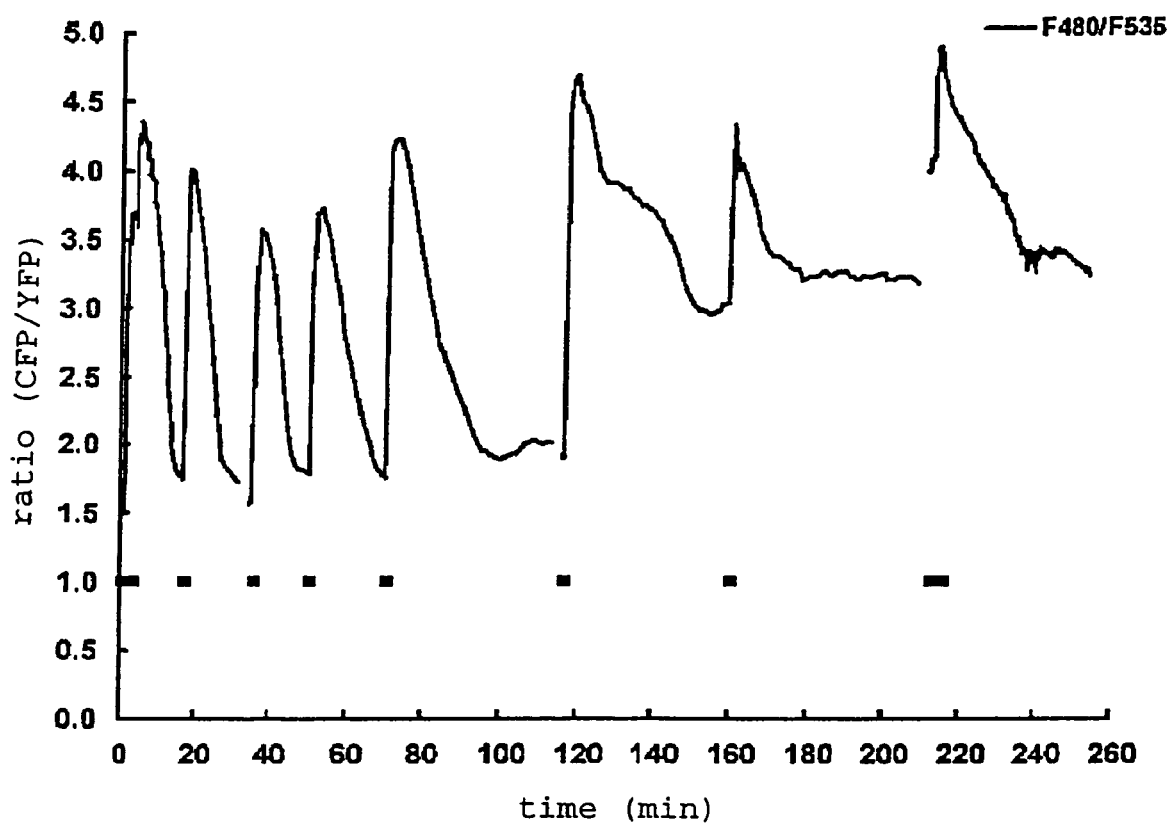
FIG. 9 shows the measurement results of FRET fluorescence ratio (ECFP/EYFP) of auditory neurons in brain slices. In the cochlear nucleus neurons expressing F2C, time-course changes in the FRET fluorescence ratio were observed. Small black bars on abscissa indicate the timing of application of KCl to the external solution (10 mM KCl stimulation).

Typical responses of fluorescence ratio (ECFP/EYFP) in FRET measurement and individual ECFP and EYFP emissions are illustrated in FIGS. 5A and 5B for cerebellar Purkinje cells in 14 days culture (14DIV), and in FIGS. 5C, 5D and FIG. 9 for cochlear nucleus neurons in a brain slice prepared from P11 rat 2 days after the injection of Sindbis-F2C.

In FIG. 5A, the fluorescence ratio sharply rises when KCl increased from the basal level of 5 mM (the timing and concentration of KCl are indicated by bars in the Figure). If F2C fusion protein had been cleaved at the calpain sensitive sequence by μ- or m-calpain, the fluorescence ratio (ECFP/EYFP) should have been maintained at a high level, since EYFP emission would have decreased; however, the fluorescence ratio decreased rapidly. The ECFP/EYFP fluorescence ratio changed 1.78-fold when the cells were exposed to 15 mM KCl, 1.39-fold to 10 mM and 1.03-fold to 7.5 mM. The emission fluorescence measured at F480 and F535 changed reciprocally. In rat brainstem slices, the FRET fluorescence ratio changed reversibly when neurons were exposed to high KCl solution (FIG. 5C). 15 mM KCl was applied 3 times and the fluorescence ratio increased rapidly each time; and the fluorescence measured at 480 nm and 535 nm changed reciprocally. In most of these measurements, the fluorescence intensity returned to the initial level after a certain time. These results were different from the observation by Vanderklish et al., wherein the YFP/CFP FRET fluorescence ratio decreased and maintained when calpain was activated by glutamatergic agonists (Vanderklish, P. W. et al., Proc. Natl. Acad. Sci. U.S.A., 97, 2253-2258, 2000).

As shown in FIG. 9, reversible changes of the ECFP/EYFP fluorescence ratio in response to the stimulation with 10 mM KCl was observed for at least 200 min.

From the above results, it was shown that F2C protein could reversibly change the fluorescence ratio in response to the cell stimulation.

(Fluorescence Properties of F2C as Intracellular Calcium Ion Indicator)

Figure 6A:
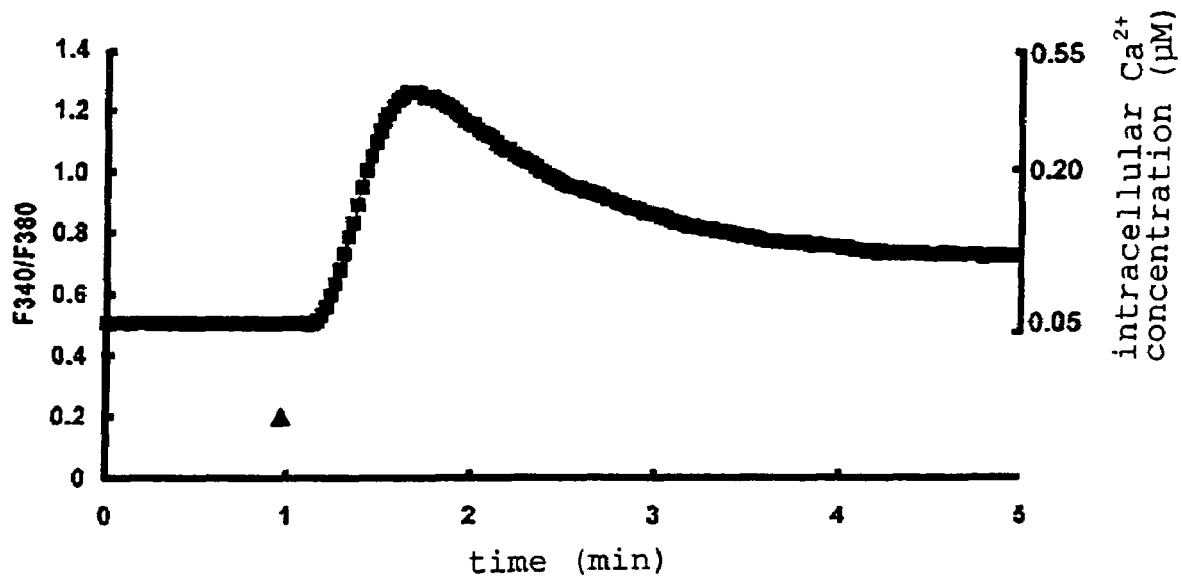
FIG. 6 shows correlated fluorescence changes of F2C with Fura-2. Time courses of the emission ratio of Fura-2(A) and F535 fluorescence intensity of F2C (B) are shown. (A) The emission ratio of F340/F380. Filled triangles indicate the timing of application of 10 mM KCl to the external solution. The scale in the right indicates the estimated intracellular $Ca^{2+}$ concentration. (B) The fluorescence intensity (F535) was normalized by the initial fluorescence $F_0$. Excitation was 440 nm.
Figure 6B:
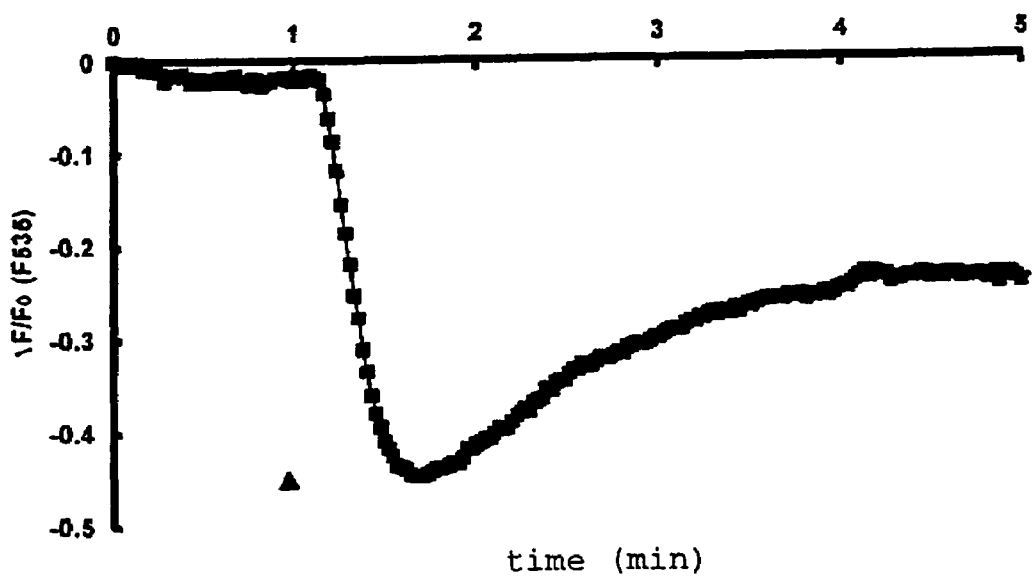

The kinetics and sensitivity to $Ca^{2+}$ of F2C were compared with those of Fura-2. FIGS. 6A and 6B show the time course changes of the fluorescence ratio of Fura-2 emission (F340/F380, FIG. 6A) and F2C (F535, FIG. 6B). Fluorescence of three wavelengths was measured by exposure time of 112 msec for each and images were sampled at the time intervals of 896 msec. When KCl was added to the recording chamber, the fluorescence change was observed with a delay of about 50 sec. This delay might have been generated by the diffusion of KCl within the recording chamber. The fluorescence of Fura-2 and F2C changed almost simultaneously.

In FIG. 6, the right scale shows intracellular $Ca^{2+}$ concentration estimated from the following calibration formula: $[Ca^{2+}]i=0.65\times(R-0.58)/(2.38-R)$. Rmax=2.38 and Rmin=0.58 were obtained by measurement from the Purkinje cell membrane loaded with Fura-2 perforated with 1 µM ionomycin, after equilibration with normal ACSF (2 mM $CaCl_2$) for Rmax and equilibration with 0 mM $CaCl_2$, 10 mM EGTA ACSF for Rmin. When measured using the Fura-2 signal, peak $Ca^{2+}$ concentration induced by $K^+$ stimulation was about 0.5 µM from the basal level of about 0.05 µM.

Figure 7:
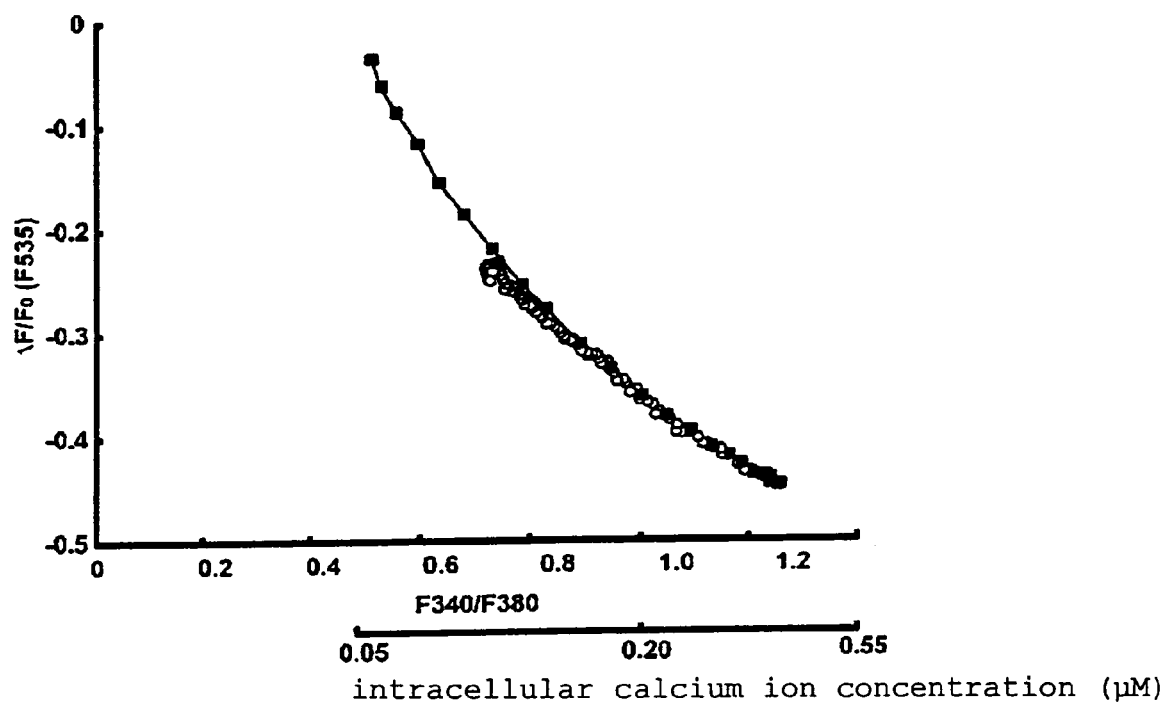
FIG. 7 shows correlated fluorescence changes of F2C with Fura-2. F535 fluorescence intensity of F2C ($\Delta F/F_0$ (F535)) was plotted against the emission ratio of Fura-2 (F340/F380) at corresponding times. Filled squares represent the rising phase of the fluorescence response and open circles to show the falling phase of the responses. The scale at the bottom side shows an intracellular $Ca^{2+}$ concentration estimated from Fura-2 ratio.
Figure 8:
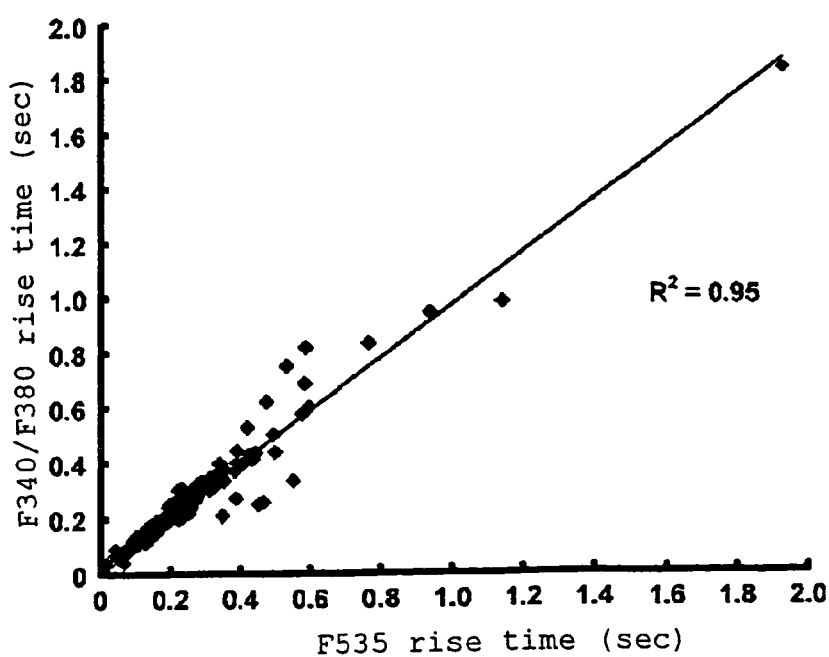
FIG. 8 shows the correlation in 20-80% rise time between the F535 fluorescence intensity of F2C ($\Delta F/F_0$ (F535)) and emission ratio of Fura-2/AM (F340/F380).

In FIG. 7, the time course changes of the fluorescence were compared by plotting F535 ($\Delta F/F_0$) versus F340/F380 at the corresponding time; wherein filled squares represent the rising phase of the response and open circles show the falling phase of the responses. Both the rising phase and the falling phase followed an overlapping trajectory. A slight downward slanting of the plot indicates larger changes in F2C than in Fura-2 signals. In FIG. 8, the rise time (20-80%) of F535 versus the rise time of F340/F380 is plotted. (These plots include experiments performed in various recording conditions; 0.5 mM, 1.0 mM, 2.0 mM $CaCl_2$ in the external medium. $Ca^{2+}$ responses were induced by the addition of KCl at the concentration of 5→10 mM, 7.5→12.5 mM, 10→20 mM. 20-80% rise time was measured and plotted for individual cells (n=240)). It showed a quasi-linear relationship (n=240 cells), indicating that $Ca^{2+}$ responses of F2C and Fura-2 were at almost the same speed.

FIGS. 6-8 indicate that the dynamic range of F2C was overlapped with that of Fura-2. The titration of F2C indicated an apparent Kd value for $Ca^{2+}$ of 150 nM and a Hill coefficient of 4 at pH 7.4.

Cerebella cultures were preincubated with calpain inhibitors (ALLN 100 µM and ALLM 50 µM) and potassium stimulation was similarly applied. The reciprocal changes of F340 and F380 Fura-2 fluorescence and the reduction of F535 EYFP fluorescence were similarly induced. The percentage of F535 EYFP maximum fluorescence change to Fura-2 maximum ratio change was not different from that of the control free of calpain inhibitors (ALLN, ALLM, ALLN+ALLM; p>0.28)(Table 1). These results indicate that calpain inhibitors were not effective.

TABLE 1

|  | Control | ALLN | ALLM | ALLN + ALLM |
|---|---|---|---|---|
| mean ± S.E.M. (%) | 36.2 ± 1.1 | 37.1 ± 2.1 | 35.9 ± 1.4 | 38.4 ± 1.6 |
| n | 10 | 10 | 10 | 10 |

Table 1 shows the percentages of F535 EYFP maximum fluorescence change to Fura-2 maximum ratio change (mean±S.E.M.), wherein n is the number of cells.

The above results reveal that F2C has almost the same calcium ion concentration sensitivity and reaction rate as those of Fura-2, as well as superior intracellular calcium ion indicator function that enables measurement of intracellular calcium ion concentration for a long time.

Example 2

In the same manner as in Example 1, an intracellular calcium ion indicator protein was designed and named as F1C. Like F2C, F1C is a fusion protein of N-terminal palmitoylation signal sequence of GAP43, ECFP, calpain sensitive sequence of α-spectrin, and EYFP. Different from F2C, F1C has one calpain sensitive sequence of α-spectrin in a linker connecting ECFP and EYFP.

The amino acid sequence of F1C is shown in SEQ ID NO:8 and the polynucleotide sequence is shown in SEQ ID NO:7. In the amino acid sequence shown by SEQ ID NO:8, amino acid position 1-20 corresponds to the palmitoylation signal sequence, amino acid position 21-26 corresponds to the linker polypeptide residue connecting the palmitoylation signal sequence and ECFP residue, amino acid position 27-265 corresponds to the ECFP residue, amino acid position 266-286 corresponds to the linker polypeptide residue connecting the ECFP residue and the EYFP residue, and amino acid position 287-525 corresponds to the EYFP residue.

An F1C construct designed as in the above was inserted into a multiple cloning site of pSinRep5 (pSindbis-F1C) in the same manner as in Example 1. In the same manner as in Example 1, RNA transcribed from pSindbis-F1C and helper RNA were transfected into BHK cells, and Sindbis virus encoding the F1C protein (Sindbis-F1C) was obtained from the culture supernatant. The obtained Sindbis-F1C was injected into the rat brain-stem in the same manner as in Example 1 for in vivo infection and brain-stem slices were prepared.

In the same manner as in Example 1, the brain-stem slices were stimulated with KCl (10 mM), and the ECFP/EYFP fluorescence ratio in the cochlear nuclei neurons in the brain-stem slices was measured over time.

Figure 10:
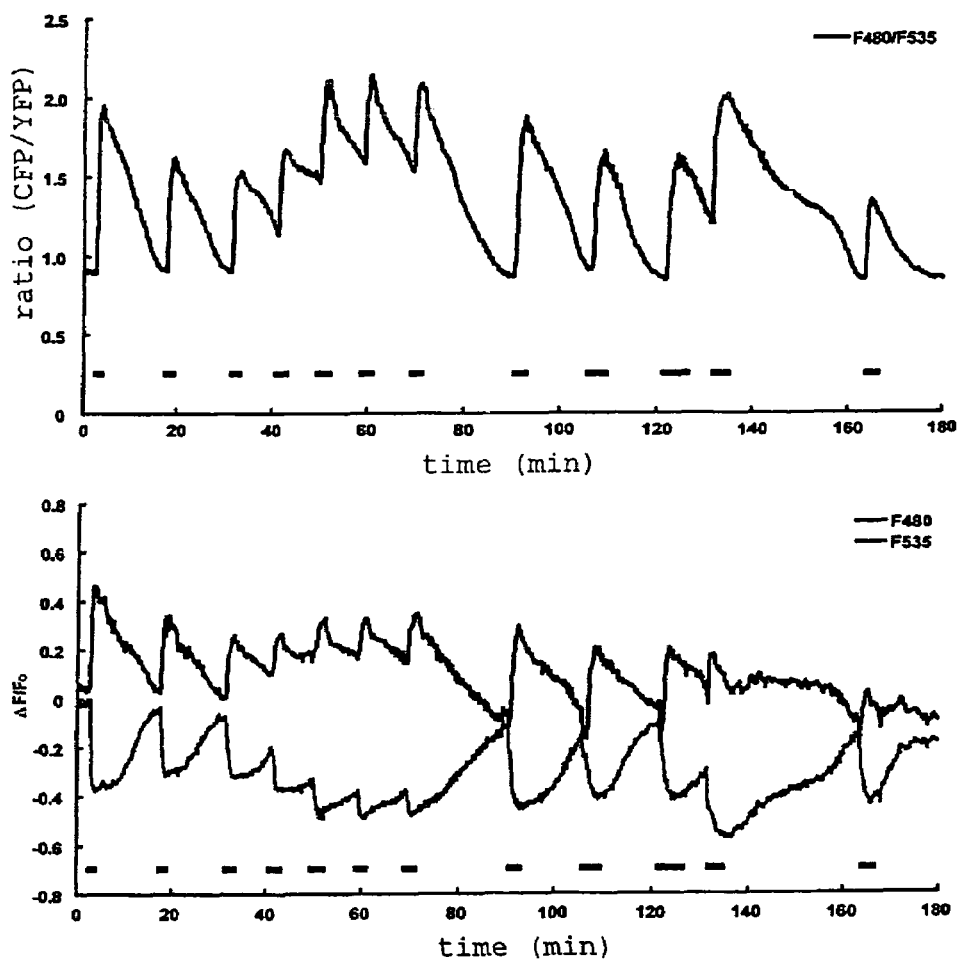
FIG. 10 shows the measurement results of FRET fluorescence ratio (ECFP/EYFP) of auditory neurons in brain-stem slices. In the cochlear nucleus neurons expressing F1C, time-course changes in the fluorescence intensity were measured. Small black bars on abscissa indicate the timing of application of KCl to the external solution (10 mM KCl stimulation). The upper panel shows changes in the FRET fluorescence ratio (ECFP/EYFP) and the lower panel shows reciprocal changes in fluorescence from ECFP (F480 nm) and EYFP (F535 nm). The fluorescence intensity of F480 and F535 were plotted after normalization by initial fluorescence intensity $F_0$.

As a result, in the case of F1C, KCl stimulation caused steep increase in the ECFP/EYFP fluorescence ratio, after which the fluorescence ratio decreased rapidly, as in the case of F2C. By repetitive stimulation of brain-stem slices with KCl, the ECFP/EYFP fluorescence ratio changed reversibly, where the fluorescence ratio rapidly increased upon each stimulation, and returned to the initial level after a certain time (FIG. 10).

From the above results, it has been shown that the polypeptide of the present invention has a superior intracellular calcium ion indicator function, irrespective of the number of calpain sensitive sequences contained in the linker polypeptide residue connecting the two fluorescent polypeptide residues.

Example 3

In the same manner as in Example 1, an intracellular calcium ion indicator protein was designed and named as Fα. Like F2C, Fα is a fusion protein of N-terminal palmitoylation signal sequence of GAP43, ECFP, two calpain sensitive sequences, and EYFP. Different from F2C, one (N-terminal side) of the two calpain sensitive sequences contained in Fα is a PKCα-derived calpain sensitive sequence (SEQ ID NO:3) and the other (C-terminal side) is a calpain sensitive sequence of α-spectrin. In the polynucleotide sequence encoding F2C, the region cleavable by XhoI is substituted by a polynucleotide sequence encoding PKCα-derived calpain sensitive sequence. The PKCα-derived calpain sensitive sequence corresponds to the V3 region of PKCα.

The amino acid sequence of Fα is shown in SEQ ID NO:10 and the polynucleotide sequence is shown in SEQ ID NO:9. In the amino acid sequence shown by SEQ ID NO:10, amino acid position 1-20 corresponds to the palmitoylation signal sequence, amino acid position 21-26 corresponds to the linker polypeptide residue connecting the palmitoylation signal sequence and ECFP residue, amino acid position 27-265 corresponds to the ECFP residue, amino acid position 266-336 corresponds to the linker polypeptide residue connecting the ECFP residue and the EYFP residue, and amino acid position 337-575 corresponds to the EYFP residue.

An Fα construct designed as in the above was inserted into a multiple cloning site of pSinRep5 (pSindbis-Fα) in the same manner as in Example 1. In the same manner as in Example 1, RNA transcribed from pSindbis-Fα and helper RNA were transfected into BHK cells, and Sindbis virus encoding the Fα protein (Sindbis-Fα) was obtained from the culture supernatant. The obtained Sindbis-Fα was injected into the rat brain-stem in the same manner as in Example 1 for in vivo infection and brain-stem slices were prepared.

In the same manner as in Example 1, the brain-stem slices were stimulated with KCl (8 mM), and the ECFP/EYFP fluorescence ratio in the cochlear nuclei neurons in the brain-stem slices was measured over time.

Figure 11:
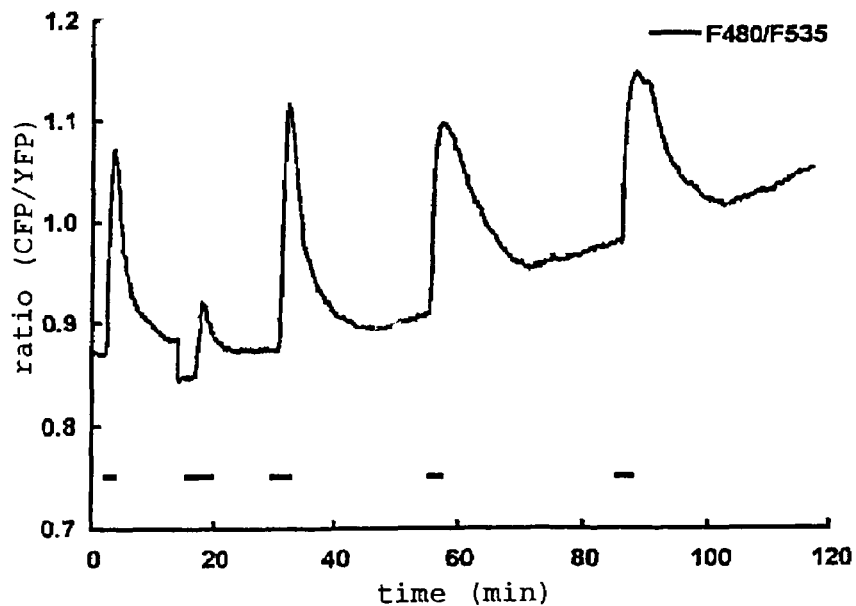
FIG. 11 shows the measurement results of FRET fluorescence ratio (ECFP/EYFP) of cochlear nucleus neurons in brain-stem slices. In the cochlear nucleus neurons expressing Fα, time-course changes in the FRET fluorescence intensity were measured. Small black bars on abscissa indicate the timing of application of KCl to the external solution (8 mM KCl stimulation).

As a result, in the case of Fα, KCl stimulation caused steep increase in the ECFP/EYFP fluorescence ratio, after which the fluorescence ratio decreased rapidly, as in the case of F2C. By repetitive stimulation of brain-stem slices with KCl, the ECFP/EYFP fluorescence ratio changed reversibly, where the fluorescence ratio rapidly increased upon each stimulation, and returned to the initial level after a certain time (FIG. 11).

From the above results, it has been shown that the polypeptide of the present invention has a superior intracellular calcium ion indicator function even when a PKCα-derived sequence is used as a calpain sensitive sequence, as in the case of sole use of α-spectrin-derived sequence.

Example 4

In the same manner as in Example 1, an intracellular calcium ion indicator protein was designed and named as Fβ. Like F2C, Fβ is a fusion protein of N-terminal palmitoylation signal sequence of GAP43, ECFP, two calpain sensitive sequences, and EYFP. Different from F2C, one (N-terminal side) of the two calpain sensitive sequences contained in Fβ is a PKCβ-derived calpain sensitive sequence (SEQ ID NO:4) and the other (C-terminal side) is a calpain sensitive sequence of α-spectrin. In the polynucleotide sequence encoding F2C, the region cleavable by XhoI is substituted by a polynucleotide sequence encoding PKCβ-derived calpain sensitive sequence. The PKCβ-derived calpain sensitive sequence corresponds to the V3 region of PKCβ.

The amino acid sequence of Fβ is shown in SEQ ID NO:12 and the polynucleotide sequence is shown in SEQ ID NO:11. In the amino acid sequence shown by SEQ ID NO:12, amino acid position 1-20 corresponds to the palmitoylation signal sequence, amino acid position 21-26 corresponds to the linker polypeptide residue connecting the palmitoylation signal sequence and ECFP residue, amino acid position 27-265 corresponds to the ECFP residue, amino acid position 266-339 corresponds to the linker polypeptide residue connecting the ECFP residue and the EYFP residue, and amino acid position 340-578 corresponds to the EYFP residue.

An Fβ construct designed as in the above was inserted into a multiple cloning site of pSinRep5 (pSindbis-Fβ) in the same manner as in Example 1. In the same manner as in Example 1, RNA transcribed from pSindbis-Fβ and helper RNA were transfected into BHK cells, and Sindbis virus encoding the Fβ protein (Sindbis-Fβ) was obtained from the culture supernatant. The obtained Sindbis-Fβ was injected into the rat brain-stem in the same manner as in Example 1 for in vivo infection and brain-stem slices were prepared.

In the same manner as in Example 1, the brain-stem slices were stimulated with KCl (10 mM), and the ECFP/EYFP fluorescence ratio in the cochlear nuclei neurons in the brain-stem slices was measured over time.

Figure 12:
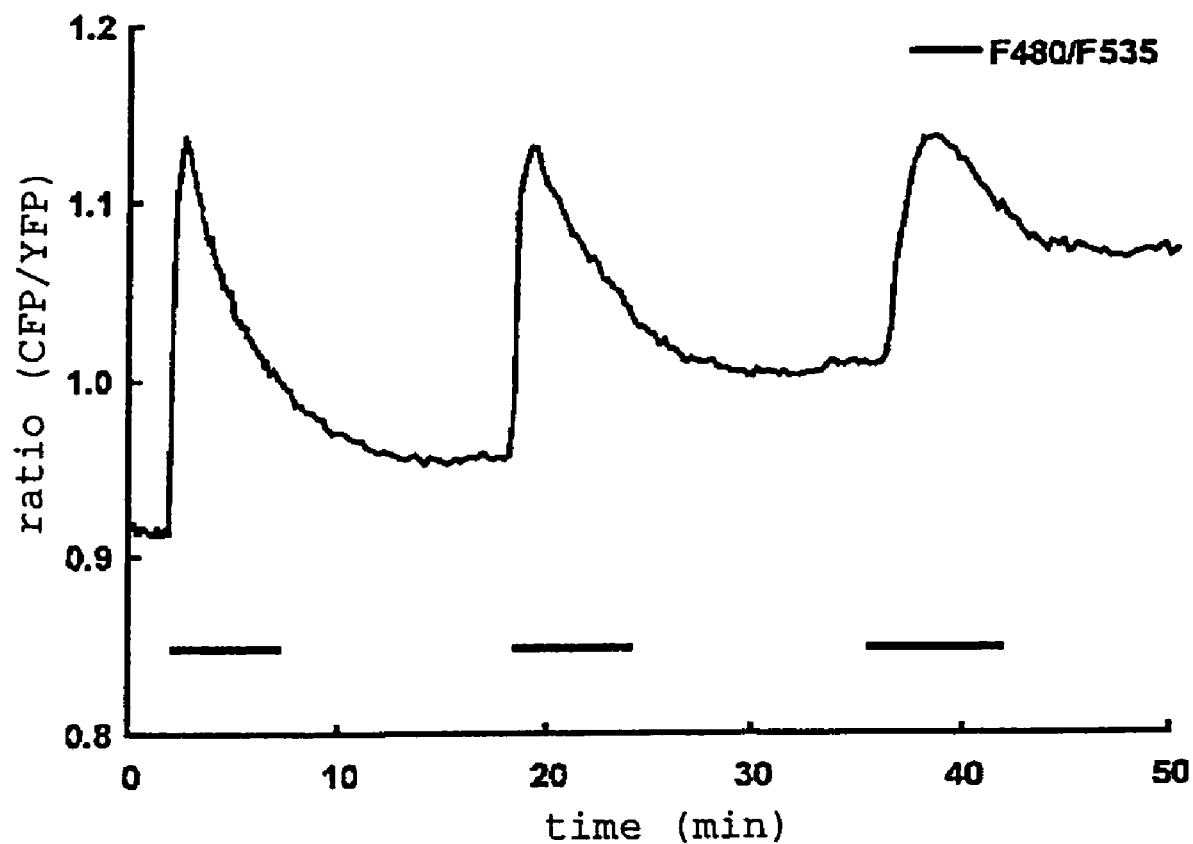
FIG. 12 shows the measurement results of FRET fluorescence ratio (ECFP/EYFP) of cochlear nucleus neurons in brain-stem slices. In the cochlear nucleus neurons expressing Fβ, time-course changes in the fluorescence intensity were measured. Small black bars on abscissa indicate the timing of application of KCl to the external solution (10 mM KCl stimulation).

As a result, in the case of Fβ, KCl stimulation caused steep increase in the ECFP/EYFP fluorescence ratio, after which the fluorescence ratio decreased rapidly, as in the case of F2C. By repetitive stimulation of brain-stem slices with KCl, the ECFP/EYFP fluorescence ratio changed reversibly, where the fluorescence ratio rapidly increased upon each stimulation, and returned to the initial level after a certain time (FIG. 12).

From the above results, it has been shown that the polypeptide of the present invention has a superior intracellular calcium ion indicator function even when a PKCβ-derived sequence is used as a calpain sensitive sequence, as in the case of sole use of α-spectrin-derived sequence.

From the above results, moreover, it has been shown that the polypeptide of the present invention can exhibit a superior intracellular calcium ion indicator function, irrespective of the kind and number of calpain sensitive sequences contained in the linker polypeptide residue connecting the two fluorescent polypeptide residues.

Sequence Listing Free Text

SEQ ID NO:1: GAP-43 palmitoylation signal

SEQ ID NO:2: calpain sensitive sequence from α-spectrin

SEQ ID NO:3: calpain sensitive sequence from PKC α

SEQ ID NO:4: calpain sensitive sequence from PKCβ

SEQ ID NO:5: F2C

SEQ ID NO:6: F2C

SEQ ID NO:7: F1C

SEQ ID NO:8: F1C

SEQ ID NO:9: Fα

SEQ ID NO:10: Fα

SEQ ID NO:11: Fβ

SEQ ID NO:12: Fβ

SEQ ID NO:13: GAP-43 palmitoylation signal (10 amino acids)

SEQ ID NO:14: c-src myristoilation signal

What is claimed is:

1. A polypeptide having an intracellular calcium ion indicator function, which comprises the following elements (a)-(c):

(a) a polypeptide residue consisting of a membrane localization signal sequence;

(b) a first fluorescent polypeptide residue; and (c) a second fluorescent polypeptide residue in the order of (a), (b) and (c) from the N-terminal side, wherein one of said two fluorescent polypeptide residues is a donor for fluorescence resonance energy transfer, the other is the corresponding acceptor, and said two fluorescent polypeptide residues are connected with a linker polypeptide residue comprising at least one calpain sensitive sequence, thereby to allow fluorescence resonance energy transfer between them, and wherein the polypeptide having an intracellular calcium ion indicator function is not cleaved by calpain at the calpain sensitive sequence in the linker polypeptide residue when expressed in a cell.

2. The polypeptide of claim 1, wherein the membrane localization signal sequence is a signal sequence capable of anchoring the polypeptide to a cell membrane via a lipid chain.

3. The polypeptide of claim 1, wherein the polypeptide residue consisting of the membrane localization signal sequence and the first fluorescent polypeptide residue are connected by a bond or a linker polypeptide residue consisting of 1-100 amino acids.

4. The polypeptide of claim 1, wherein the donor for the fluorescence resonance energy transfer is a Cyan Fluorescent Protein (CFP) residue and the corresponding acceptor is a Yellow Fluorescent Protein (YFP) residue.

5. The polypeptide of claim 1, wherein the calpain sensitive sequence is a µ-calpain sensitive sequence.

6. The polypeptide of claim 1, wherein the calpain sensitive sequence consists of a partial sequence of an amino acid sequence shown by SEQ ID NO:2, SEQ ID NO:3 or SEQ ID NO:4, which has a length of not less than 6 amino acids and calpain sensitivity.

7. The polypeptide of claim 1, wherein the linker polypeptide residue has a length of not more than 200 amino acids.

8. The polypeptide of claim 1, which consists of an amino acid sequence shown by SEQ ID NO:6.

9. An intracellular calcium ion indicator consisting of a polypeptide having an intracellular calcium ion indicator function, wherein said polypeptide comprises the following elements (a)-(c):

(a) a polypeptide residue consisting of a membrane localization signal sequence;

(b) a first fluorescent polypeptide residue; and (c) a second fluorescent polypeptide residue in the order of (a), (b) and (c) from the N-terminal side, wherein one of said two fluorescent polypeptide residues is a donor for fluorescence resonance energy transfer, the other is the corresponding acceptor, and said two fluorescent polypeptide residues are connected with a linker polypeptide residue comprising at least one calpain sensitive sequence, thereby to allow fluorescence resonance energy transfer between them, and wherein the polypeptide having an intracellular calcium ion indicator function is not cleaved by calpain at the calpain sensitive sequence in the linker polypeptide residue when expressed in a cell.

10. A method of measuring an intracellular calcium ion concentration, which comprises the following steps of:

(A) providing a cell comprising a polypeptide having an intracellular calcium ion indicator function, wherein the polypeptide comprises the following elements (a)-(c):

(a) a polypeptide residue consisting of a membrane localization signal sequence;

(b) a first fluorescent polypeptide residue; and (c) a second fluorescent polypeptide residue in the order of (a), (b) and (c) from the N-terminal side, wherein one of said two fluorescent polypeptide residues is a donor for fluorescence resonance energy transfer, the other is the corresponding acceptor, and said two fluorescent polypeptide residues are connected with a linker polypeptide residue comprising at least one calpain sensitive sequence, thereby to allow fluorescence resonance energy transfer between them, and wherein the polypeptide having an intracellular calcium ion indicator function is not cleaved by calpain at the calpain sensitive sequence in the linker polypeptide residue expressed in a cell; and (B) irradiating an excitation light for said donor for the fluorescence resonance energy transfer, to the cell provided in step (A), and measuring the level of the fluorescence resonance energy transfer.

* * * * *

SEQUENCE LISTING

<160> NUMBER OF SEQ ID NOS: 14

<210> SEQ ID NO 1
<211> LENGTH: 20
<212> TYPE: PRT
<213> ORGANISM: Artificial
<220> FEATURE:
<223> OTHER INFORMATION: GAP-43 palmitoylation signal

<400> SEQUENCE: 1

Met Leu Cys Cys Met Arg Arg Thr Lys Gln Val Glu Lys Asn Asp Glu
1               5                   10                  15

Asp Gln Lys Ile
            20

<210> SEQ ID NO 2
<211> LENGTH: 19
<212> TYPE: PRT
<213> ORGANISM: Artificial
<220> FEATURE:
<223> OTHER INFORMATION: calpain sensitive sequence from alpha-spectrin

<400> SEQUENCE: 2

Gly Ser Gly Ser Gly Gln Gln Glu Val Tyr Gly Met Met Pro Arg Asp
1               5                   10                  15

Gly Ser Gly

<210> SEQ ID NO 3
<211> LENGTH: 48
<212> TYPE: PRT
<213> ORGANISM: Artificial
<220> FEATURE:
<223> OTHER INFORMATION: calpain sensitive sequence from PKC-alpha

<400> SEQUENCE: 3

Ile Pro Glu Gly Asp Glu Glu Gly Asn Met Glu Leu Arg Gln Lys Phe
1               5                   10                  15

Glu Lys Ala Lys Leu Gly Pro Val Gly Asn Lys Val Ile Ser Pro Ser
            20                  25                  30

Glu Asp Arg Lys Gln Pro Ser Asn Asn Leu Asp Arg Val Lys Leu Thr
        35                  40                  45

<210> SEQ ID NO 4
<211> LENGTH: 51
<212> TYPE: PRT
<213> ORGANISM: Artificial
<220> FEATURE:
<223> OTHER INFORMATION: calpain sensitive sequence from PKC-beta

<400> SEQUENCE: 4

Val Pro Pro Glu Gly Ser Glu Gly Asn Glu Glu Leu Arg Gln Lys Phe
1               5                   10                  15

Glu Arg Ala Lys Ile Gly Gln Gly Thr Lys Ala Pro Glu Glu Lys Thr
            20                  25                  30

Ala Asn Thr Ile Ser Lys Phe Asp Asn Asn Gly Asn Arg Asp Arg Met
        35                  40                  45

Lys Leu Thr
    50

<210> SEQ ID NO 5
<211> LENGTH: 1641

```
<212> TYPE: DNA
<213> ORGANISM: Artificial
<220> FEATURE:
<223> OTHER INFORMATION: F2C
<220> FEATURE:
<221> NAME/KEY: CDS
<222> LOCATION: (1)..(1641)

<400> SEQUENCE: 5
```

| | | | | | | | | | | | | | | | | |
|---|---|---|---|---|---|---|---|---|---|---|---|---|---|---|---|---|
| atg | ctg | tgc | tgc | atg | cga | aga | acc | aaa | cag | gtt | gaa | aag | aat | gat | gag | 48 |
| Met | Leu | Cys | Cys | Met | Arg | Arg | Thr | Lys | Gln | Val | Glu | Lys | Asn | Asp | Glu | |
| 1 | | | | 5 | | | | | 10 | | | | | 15 | | |
| gac | caa | aag | atc | cac | cgg | ccg | gtc | gcc | acc | atg | gtg | agc | aag | ggc | gag | 96 |
| Asp | Gln | Lys | Ile | His | Arg | Pro | Val | Ala | Thr | Met | Val | Ser | Lys | Gly | Glu | |
| | | | 20 | | | | | 25 | | | | | 30 | | | |
| gag | ctg | ttc | acc | ggg | gtg | gtc | ccc | atc | ctg | gtc | gag | ctg | gac | ggc | gac | 144 |
| Glu | Leu | Phe | Thr | Gly | Val | Val | Pro | Ile | Leu | Val | Glu | Leu | Asp | Gly | Asp | |
| | | 35 | | | | | 40 | | | | | 45 | | | | |
| gta | aac | ggc | cac | aag | ttc | agc | gtg | tcc | ggc | gag | ggc | gag | ggc | gat | gcc | 192 |
| Val | Asn | Gly | His | Lys | Phe | Ser | Val | Ser | Gly | Glu | Gly | Glu | Gly | Asp | Ala | |
| | 50 | | | | | 55 | | | | | 60 | | | | | |
| acc | tac | ggc | aag | ctg | acc | ctg | aag | ttc | atc | tgc | acc | acc | ggc | aag | ctg | 240 |
| Thr | Tyr | Gly | Lys | Leu | Thr | Leu | Lys | Phe | Ile | Cys | Thr | Thr | Gly | Lys | Leu | |
| 65 | | | | | 70 | | | | | 75 | | | | | 80 | |
| ccc | gtg | ccc | tgg | ccc | acc | ctc | gtg | acc | acc | ctg | acc | tgg | ggc | gtg | cag | 288 |
| Pro | Val | Pro | Trp | Pro | Thr | Leu | Val | Thr | Thr | Leu | Thr | Trp | Gly | Val | Gln | |
| | | | | 85 | | | | | 90 | | | | | 95 | | |
| tgc | ttc | agc | cgc | tac | ccc | gac | cac | atg | aag | cag | cac | gac | ttc | ttc | aag | 336 |
| Cys | Phe | Ser | Arg | Tyr | Pro | Asp | His | Met | Lys | Gln | His | Asp | Phe | Phe | Lys | |
| | | | 100 | | | | | 105 | | | | | 110 | | | |
| tcc | gcc | atg | ccc | gaa | ggc | tac | gtc | cag | gag | cgc | acc | atc | ttc | ttc | aag | 384 |
| Ser | Ala | Met | Pro | Glu | Gly | Tyr | Val | Gln | Glu | Arg | Thr | Ile | Phe | Phe | Lys | |
| | | | 115 | | | | | 120 | | | | | 125 | | | |
| gac | gac | ggc | aac | tac | aag | acc | cgc | gcc | gag | gtg | aag | ttc | gag | ggc | gac | 432 |
| Asp | Asp | Gly | Asn | Tyr | Lys | Thr | Arg | Ala | Glu | Val | Lys | Phe | Glu | Gly | Asp | |
| | | 130 | | | | | 135 | | | | | 140 | | | | |
| acc | ctg | gtg | aac | cgc | atc | gag | ctg | aag | ggc | atc | gac | ttc | aag | gag | gac | 480 |
| Thr | Leu | Val | Asn | Arg | Ile | Glu | Leu | Lys | Gly | Ile | Asp | Phe | Lys | Glu | Asp | |
| 145 | | | | | 150 | | | | | 155 | | | | | 160 | |
| ggc | aac | atc | ctg | ggg | cac | aag | ctg | gag | tac | aac | tac | atc | agc | cac | aac | 528 |
| Gly | Asn | Ile | Leu | Gly | His | Lys | Leu | Glu | Tyr | Asn | Tyr | Ile | Ser | His | Asn | |
| | | | | 165 | | | | | 170 | | | | | 175 | | |
| gtc | tat | atc | acc | gcc | gac | aag | cag | aag | aac | ggc | atc | aag | gcc | aac | ttc | 576 |
| Val | Tyr | Ile | Thr | Ala | Asp | Lys | Gln | Lys | Asn | Gly | Ile | Lys | Ala | Asn | Phe | |
| | | | 180 | | | | | 185 | | | | | 190 | | | |
| aag | atc | cgc | cac | aac | atc | gag | gac | ggc | agc | gtg | cag | ctc | gcc | gac | cac | 624 |
| Lys | Ile | Arg | His | Asn | Ile | Glu | Asp | Gly | Ser | Val | Gln | Leu | Ala | Asp | His | |
| | | | 195 | | | | | 200 | | | | | 205 | | | |
| tac | cag | cag | aac | acc | ccc | atc | ggc | gac | ggc | ccc | gtg | ctg | ctg | ccc | gac | 672 |
| Tyr | Gln | Gln | Asn | Thr | Pro | Ile | Gly | Asp | Gly | Pro | Val | Leu | Leu | Pro | Asp | |
| | 210 | | | | | 215 | | | | | 220 | | | | | |
| aac | cac | tac | ctg | agc | acc | cag | tcc | gcc | ctg | agc | aaa | gac | ccc | aac | gag | 720 |
| Asn | His | Tyr | Leu | Ser | Thr | Gln | Ser | Ala | Leu | Ser | Lys | Asp | Pro | Asn | Glu | |
| 225 | | | | | 230 | | | | | 235 | | | | | 240 | |
| aag | cgc | gat | cac | atg | gtc | ctg | ctg | gag | ttc | gtg | acc | gcc | gcc | ggg | atc | 768 |
| Lys | Arg | Asp | His | Met | Val | Leu | Leu | Glu | Phe | Val | Thr | Ala | Ala | Gly | Ile | |
| | | | | 245 | | | | | 250 | | | | | 255 | | |
| act | ctc | ggc | atg | gac | gag | ctg | tac | aag | ctc | gag | ggc | tcc | ggt | tct | ggt | 816 |
| Thr | Leu | Gly | Met | Asp | Glu | Leu | Tyr | Lys | Leu | Glu | Gly | Ser | Gly | Ser | Gly | |
| | | | 260 | | | | | 265 | | | | | 270 | | | |
| cag | cag | gaa | gtc | tac | ggt | atg | atg | cct | cgt | gat | ggt | tct | ggt | ctc | gag | 864 |

```
                                          -continued

Gln Gln Glu Val Tyr Gly Met Met Pro Arg Asp Gly Ser Gly Leu Glu
        275                 280                 285 ggc tcc ggt tct ggt cag cag gaa gtc tac ggt atg atg cct cgt gat      912
Gly Ser Gly Ser Gly Gln Gln Glu Val Tyr Gly Met Met Pro Arg Asp
290                 295                 300 ggt tct ggt atg gtg agc aag ggc gag gag ctg ttc acc ggg gtg gtg      960
Gly Ser Gly Met Val Ser Lys Gly Glu Glu Leu Phe Thr Gly Val Val
305                 310                 315                 320 ccc atc ctg gtc gag ctg gac ggc gac gta aac ggc cac aag ttc agc     1008
Pro Ile Leu Val Glu Leu Asp Gly Asp Val Asn Gly His Lys Phe Ser
                325                 330                 335 gtg tcc ggc gag ggc gag ggc gat gcc acc tac ggc aag ctg acc ctg     1056
Val Ser Gly Glu Gly Glu Gly Asp Ala Thr Tyr Gly Lys Leu Thr Leu
            340                 345                 350 aag ttc atc tgc acc acc ggc aag ctg ccc gtg ccc tgg ccc acc ctc     1104
Lys Phe Ile Cys Thr Thr Gly Lys Leu Pro Val Pro Trp Pro Thr Leu
        355                 360                 365 gtg acc acc ttc ggc tac ggc ctg cag tgc ttc gcc cgc tac ccc gac     1152
Val Thr Thr Phe Gly Tyr Gly Leu Gln Cys Phe Ala Arg Tyr Pro Asp
    370                 375                 380 cac atg aag cag cac gac ttc ttc aag tcc gcc atg ccc gaa ggc tac     1200
His Met Lys Gln His Asp Phe Phe Lys Ser Ala Met Pro Glu Gly Tyr
385                 390                 395                 400 gtc cag gag cgc acc atc ttc ttc aag gac gac ggc aac tac aag acc     1248
Val Gln Glu Arg Thr Ile Phe Phe Lys Asp Asp Gly Asn Tyr Lys Thr
                405                 410                 415 cgc gcc gag gtg aag ttc gag ggc gac acc ctg gtg aac cgc atc gag     1296
Arg Ala Glu Val Lys Phe Glu Gly Asp Thr Leu Val Asn Arg Ile Glu
            420                 425                 430 ctg aag ggc atc gac ttc aag gag gac ggc aac atc ctg ggg cac aag     1344
Leu Lys Gly Ile Asp Phe Lys Glu Asp Gly Asn Ile Leu Gly His Lys
        435                 440                 445 ctg gag tac aac tac aac agc cac aac gtc tat atc atg gcc gac aag     1392
Leu Glu Tyr Asn Tyr Asn Ser His Asn Val Tyr Ile Met Ala Asp Lys
    450                 455                 460 cag aag aac ggc atc aag gtg aac ttc aag atc cgc cac aac atc gag     1440
Gln Lys Asn Gly Ile Lys Val Asn Phe Lys Ile Arg His Asn Ile Glu
465                 470                 475                 480 gac ggc agc gtg cag ctc gcc gac cac tac cag cag aac acc ccc atc     1488
Asp Gly Ser Val Gln Leu Ala Asp His Tyr Gln Gln Asn Thr Pro Ile
                485                 490                 495 ggc gac ggc ccc gtg ctg ctg ccc gac aac cac tac ctg agc tac cag     1536
Gly Asp Gly Pro Val Leu Leu Pro Asp Asn His Tyr Leu Ser Tyr Gln
            500                 505                 510 tcc gcc ctg agc aaa gac ccc aac gag aag cgc gat cac atg gtc ctg     1584
Ser Ala Leu Ser Lys Asp Pro Asn Glu Lys Arg Asp His Met Val Leu
        515                 520                 525 ctg gag ttc gtg acc gcc gcc ggg atc act ctc ggc atg gac gag ctg     1632
Leu Glu Phe Val Thr Ala Ala Gly Ile Thr Leu Gly Met Asp Glu Leu
    530                 535                 540 tac aag taa                                                          1641
Tyr Lys
545

<210> SEQ ID NO 6
<211> LENGTH: 546
<212> TYPE: PRT
<213> ORGANISM: Artificial
<220> FEATURE:
<223> OTHER INFORMATION: F2C
```

<400> SEQUENCE: 6

```
Met Leu Cys Cys Met Arg Arg Thr Lys Gln Val Glu Lys Asn Asp Glu
1               5                   10                  15

Asp Gln Lys Ile His Arg Pro Val Ala Thr Met Val Ser Lys Gly Glu
            20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
    50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Trp Gly Val Gln
                85                  90                  95

Cys Phe Ser Arg Tyr Pro Asp His Met Lys Gln His Asp Phe Phe Lys
            100                 105                 110

Ser Ala Met Pro Glu Gly Tyr Val Gln Glu Arg Thr Ile Phe Phe Lys
            115                 120                 125

Asp Asp Gly Asn Tyr Lys Thr Arg Ala Glu Val Lys Phe Glu Gly Asp
130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Ile Ser His Asn
                165                 170                 175

Val Tyr Ile Thr Ala Asp Lys Gln Lys Asn Gly Ile Lys Ala Asn Phe
            180                 185                 190

Lys Ile Arg His Asn Ile Glu Asp Gly Ser Val Gln Leu Ala Asp His
            195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys Leu Glu Gly Ser Gly Ser Gly
            260                 265                 270

Gln Gln Glu Val Tyr Gly Met Met Pro Arg Asp Gly Ser Gly Leu Glu
            275                 280                 285

Gly Ser Gly Ser Gly Gln Gln Glu Val Tyr Gly Met Met Pro Arg Asp
    290                 295                 300

Gly Ser Gly Met Val Ser Lys Gly Glu Glu Leu Phe Thr Gly Val Val
305                 310                 315                 320

Pro Ile Leu Val Glu Leu Asp Gly Asp Val Asn Gly His Lys Phe Ser
                325                 330                 335

Val Ser Gly Glu Gly Glu Gly Asp Ala Thr Tyr Gly Lys Leu Thr Leu
            340                 345                 350

Lys Phe Ile Cys Thr Thr Gly Lys Leu Pro Val Pro Trp Pro Thr Leu
            355                 360                 365

Val Thr Thr Phe Gly Tyr Gly Leu Gln Cys Phe Ala Arg Tyr Pro Asp
    370                 375                 380

His Met Lys Gln His Asp Phe Phe Lys Ser Ala Met Pro Glu Gly Tyr
385                 390                 395                 400

Val Gln Glu Arg Thr Ile Phe Phe Lys Asp Asp Gly Asn Tyr Lys Thr
                405                 410                 415
```

-continued

```
Arg Ala Glu Val Lys Phe Glu Gly Asp Thr Leu Val Asn Arg Ile Glu
            420                 425                 430

Leu Lys Gly Ile Asp Phe Lys Glu Asp Gly Asn Ile Leu Gly His Lys
        435                 440                 445

Leu Glu Tyr Asn Tyr Asn Ser His Asn Val Tyr Ile Met Ala Asp Lys
    450                 455                 460

Gln Lys Asn Gly Ile Lys Val Asn Phe Lys Ile Arg His Asn Ile Glu
465                 470                 475                 480

Asp Gly Ser Val Gln Leu Ala Asp His Tyr Gln Gln Asn Thr Pro Ile
                485                 490                 495

Gly Asp Gly Pro Val Leu Leu Pro Asp Asn His Tyr Leu Ser Tyr Gln
            500                 505                 510

Ser Ala Leu Ser Lys Asp Pro Asn Glu Lys Arg Asp His Met Val Leu
        515                 520                 525

Leu Glu Phe Val Thr Ala Ala Gly Ile Thr Leu Gly Met Asp Glu Leu
    530                 535                 540

Tyr Lys
545

<210> SEQ ID NO 7
<211> LENGTH: 1578
<212> TYPE: DNA
<213> ORGANISM: Artificial
<220> FEATURE:
<223> OTHER INFORMATION: F1C
<220> FEATURE:
<221> NAME/KEY: CDS
<222> LOCATION: (1)..(1578)

<400> SEQUENCE: 7 atg ctg tgc tgc atg cga aga acc aaa cag gtt gaa aag aat gat gag    48
Met Leu Cys Cys Met Arg Arg Thr Lys Gln Val Glu Lys Asn Asp Glu
1               5                   10                  15 gac caa aag atc cac cgg ccg gtc gcc acc atg gtg agc aag ggc gag    96
Asp Gln Lys Ile His Arg Pro Val Ala Thr Met Val Ser Lys Gly Glu
                20                  25                  30 gag ctg ttc acc ggg gtg gtg ccc atc ctg gtc gag ctg gac ggc gac   144
Glu Leu Phe Thr Gly Val Val Pro Ile Leu Val Glu Leu Asp Gly Asp
            35                  40                  45 gta aac ggc cac aag ttc agc gtg tcc ggc gag ggc gag ggc gat gcc   192
Val Asn Gly His Lys Phe Ser Val Ser Gly Glu Gly Glu Gly Asp Ala
        50                  55                  60 acc tac ggc aag ctg acc ctg aag ttc atc tgc acc acc ggc aag ctg   240
Thr Tyr Gly Lys Leu Thr Leu Lys Phe Ile Cys Thr Thr Gly Lys Leu
65                  70                  75                  80 ccc gtg ccc tgg ccc acc ctc gtg acc acc ctg acc tgg ggc gtg cag   288
Pro Val Pro Trp Pro Thr Leu Val Thr Thr Leu Thr Trp Gly Val Gln
                85                  90                  95 tgc ttc agc cgc tac ccc gac cac atg aag cag cac gac ttc ttc aag   336
Cys Phe Ser Arg Tyr Pro Asp His Met Lys Gln His Asp Phe Phe Lys
                100                 105                 110 tcc gcc atg ccc gaa ggc tac gtc cag gag cgc acc atc ttc ttc aag   384
Ser Ala Met Pro Glu Gly Tyr Val Gln Glu Arg Thr Ile Phe Phe Lys
            115                 120                 125 gac gac ggc aac tac aag acc cgc gcc gag gtg aag ttc gag ggc gac   432
Asp Asp Gly Asn Tyr Lys Thr Arg Ala Glu Val Lys Phe Glu Gly Asp
        130                 135                 140 acc ctg gtg aac cgc atc gag ctg aag ggc atc gac ttc aag gag gac   480
Thr Leu Val Asn Arg Ile Glu Leu Lys Gly Ile Asp Phe Lys Glu Asp
```

-continued

```
                        145                 150                 155                 160
ggc aac atc ctg ggg cac aag ctg gag tac aac tac atc agc cac aac         528
Gly Asn Ile Leu Gly His Lys Leu Glu Tyr Asn Tyr Ile Ser His Asn
                165                 170                 175 gtc tat atc acc gcc gac aag cag aag aac ggc atc aag gcc aac ttc         576
Val Tyr Ile Thr Ala Asp Lys Gln Lys Asn Gly Ile Lys Ala Asn Phe
            180                 185                 190 aag atc cgc cac aac atc gag gac ggc agc gtg cag ctc gcc gac cac         624
Lys Ile Arg His Asn Ile Glu Asp Gly Ser Val Gln Leu Ala Asp His
        195                 200                 205 tac cag cag aac acc ccc atc ggc gac ggc ccc gtg ctg ctg ccc gac         672
Tyr Gln Gln Asn Thr Pro Ile Gly Asp Gly Pro Val Leu Leu Pro Asp
    210                 215                 220 aac cac tac ctg agc acc cag tcc gcc ctg agc aaa gac ccc aac gag         720
Asn His Tyr Leu Ser Thr Gln Ser Ala Leu Ser Lys Asp Pro Asn Glu
225                 230                 235                 240 aag cgc gat cac atg gtc ctg ctg gag ttc gtg acc gcc gcc ggg atc         768
Lys Arg Asp His Met Val Leu Leu Glu Phe Val Thr Ala Ala Gly Ile
                245                 250                 255 act ctc ggc atg gac gag ctg tac aag ctc gag ggc tcc ggt tct ggt         816
Thr Leu Gly Met Asp Glu Leu Tyr Lys Leu Glu Gly Ser Gly Ser Gly
            260                 265                 270 cag cag gaa gtc tac ggt atg atg cct cgt gat ggt tct ggt atg gtg         864
Gln Gln Glu Val Tyr Gly Met Met Pro Arg Asp Gly Ser Gly Met Val
        275                 280                 285 agc aag ggc gag gag ctg ttc acc ggg gtg gtg ccc atc ctg gtc gag         912
Ser Lys Gly Glu Glu Leu Phe Thr Gly Val Val Pro Ile Leu Val Glu
    290                 295                 300 ctg gac ggc gac gta aac ggc cac aag ttc agc gtg tcc ggc gag ggc         960
Leu Asp Gly Asp Val Asn Gly His Lys Phe Ser Val Ser Gly Glu Gly
305                 310                 315                 320 gag ggc gat gcc acc tac ggc aag ctg acc ctg aag ttc atc tgc acc        1008
Glu Gly Asp Ala Thr Tyr Gly Lys Leu Thr Leu Lys Phe Ile Cys Thr
                325                 330                 335 acc ggc aag ctg ccc gtg ccc tgg ccc acc ctc gtg acc acc ttc ggc        1056
Thr Gly Lys Leu Pro Val Pro Trp Pro Thr Leu Val Thr Thr Phe Gly
            340                 345                 350 tac ggc ctg cag tgc ttc gcc cgc tac ccc gac cac atg aag cag cac        1104
Tyr Gly Leu Gln Cys Phe Ala Arg Tyr Pro Asp His Met Lys Gln His
        355                 360                 365 gac ttc ttc aag tcc gcc atg ccc gaa ggc tac gtc cag gag cgc acc        1152
Asp Phe Phe Lys Ser Ala Met Pro Glu Gly Tyr Val Gln Glu Arg Thr
    370                 375                 380 atc ttc ttc aag gac gac ggc aac tac aag acc cgc gcc gag gtg aag        1200
Ile Phe Phe Lys Asp Asp Gly Asn Tyr Lys Thr Arg Ala Glu Val Lys
385                 390                 395                 400 ttc gag ggc gac acc ctg gtg aac cgc atc gag ctg aag ggc atc gac        1248
Phe Glu Gly Asp Thr Leu Val Asn Arg Ile Glu Leu Lys Gly Ile Asp
                405                 410                 415 ttc aag gag gac ggc aac atc ctg ggg cac aag ctg gag tac aac tac        1296
Phe Lys Glu Asp Gly Asn Ile Leu Gly His Lys Leu Glu Tyr Asn Tyr
            420                 425                 430 aac agc cac aac gtc tat atc atg gcc gac aag cag aag aac ggc atc        1344
Asn Ser His Asn Val Tyr Ile Met Ala Asp Lys Gln Lys Asn Gly Ile
        435                 440                 445 aag gtg aac ttc aag atc cgc cac aac atc gag gac ggc agc gtg cag        1392
Lys Val Asn Phe Lys Ile Arg His Asn Ile Glu Asp Gly Ser Val Gln
    450                 455                 460 ctc gcc gac cac tac cag cag aac acc ccc atc ggc gac ggc ccc gtg        1440
Leu Ala Asp His Tyr Gln Gln Asn Thr Pro Ile Gly Asp Gly Pro Val
```

```
Leu Ala Asp His Tyr Gln Gln Asn Thr Pro Ile Gly Asp Gly Pro Val
465                 470                 475                 480 ctg ctg ccc gac aac cac tac ctg agc tac cag tcc gcc ctg agc aaa    1488
Leu Leu Pro Asp Asn His Tyr Leu Ser Tyr Gln Ser Ala Leu Ser Lys
                    485                 490                 495 gac ccc aac gag aag cgc gat cac atg gtc ctg ctg gag ttc gtg acc    1536
Asp Pro Asn Glu Lys Arg Asp His Met Val Leu Leu Glu Phe Val Thr
                500                 505                 510 gcc gcc ggg atc act ctc ggc atg gac gag ctg tac aag taa            1578
Ala Ala Gly Ile Thr Leu Gly Met Asp Glu Leu Tyr Lys
                515                 520                 525

<210> SEQ ID NO 8
<211> LENGTH: 525
<212> TYPE: PRT
<213> ORGANISM: Artificial
<220> FEATURE:
<223> OTHER INFORMATION: F1C

<400> SEQUENCE: 8

Met Leu Cys Cys Met Arg Arg Thr Lys Gln Val Glu Lys Asn Asp Glu
1               5                   10                  15

Asp Gln Lys Ile His Arg Pro Val Ala Thr Met Val Ser Lys Gly Glu
                20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
        50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Trp Gly Val Gln
                85                  90                  95

Cys Phe Ser Arg Tyr Pro Asp His Met Lys Gln His Asp Phe Phe Lys
            100                 105                 110

Ser Ala Met Pro Glu Gly Tyr Val Gln Glu Arg Thr Ile Phe Phe Lys
        115                 120                 125

Asp Asp Gly Asn Tyr Lys Thr Arg Ala Glu Val Lys Phe Glu Gly Asp
    130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Ile Ser His Asn
                165                 170                 175

Val Tyr Ile Thr Ala Asp Lys Gln Lys Asn Gly Ile Lys Ala Asn Phe
            180                 185                 190

Lys Ile Arg His Asn Ile Glu Asp Gly Ser Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys Leu Glu Gly Ser Gly Ser Gly
            260                 265                 270

Gln Gln Glu Val Tyr Gly Met Met Pro Arg Asp Gly Ser Gly Met Val
        275                 280                 285
```

```
Ser Lys Gly Glu Glu Leu Phe Thr Gly Val Val Pro Ile Leu Val Glu
    290                 295                 300

Leu Asp Gly Asp Val Asn Gly His Lys Phe Ser Val Ser Gly Glu Gly
305                 310                 315                 320

Glu Gly Asp Ala Thr Tyr Gly Lys Leu Thr Leu Lys Phe Ile Cys Thr
                325                 330                 335

Thr Gly Lys Leu Pro Val Pro Trp Pro Thr Leu Val Thr Thr Phe Gly
            340                 345                 350

Tyr Gly Leu Gln Cys Phe Ala Arg Tyr Pro Asp His Met Lys Gln His
        355                 360                 365

Asp Phe Phe Lys Ser Ala Met Pro Glu Gly Tyr Val Gln Glu Arg Thr
    370                 375                 380

Ile Phe Phe Lys Asp Asp Gly Asn Tyr Lys Thr Arg Ala Glu Val Lys
385                 390                 395                 400

Phe Glu Gly Asp Thr Leu Val Asn Arg Ile Glu Leu Lys Gly Ile Asp
                405                 410                 415

Phe Lys Glu Asp Gly Asn Ile Leu Gly His Lys Leu Glu Tyr Asn Tyr
            420                 425                 430

Asn Ser His Asn Val Tyr Ile Met Ala Asp Lys Gln Lys Asn Gly Ile
        435                 440                 445

Lys Val Asn Phe Lys Ile Arg His Asn Ile Glu Asp Gly Ser Val Gln
    450                 455                 460

Leu Ala Asp His Tyr Gln Gln Asn Thr Pro Ile Gly Asp Gly Pro Val
465                 470                 475                 480

Leu Leu Pro Asp Asn His Tyr Leu Ser Tyr Gln Ser Ala Leu Ser Lys
                485                 490                 495

Asp Pro Asn Glu Lys Arg Asp His Met Val Leu Leu Glu Phe Val Thr
            500                 505                 510

Ala Ala Gly Ile Thr Leu Gly Met Asp Glu Leu Tyr Lys
        515                 520                 525

<210> SEQ ID NO 9
<211> LENGTH: 1728
<212> TYPE: DNA
<213> ORGANISM: Artificial
<220> FEATURE:
<223> OTHER INFORMATION: F alpha
<220> FEATURE:
<221> NAME/KEY: CDS
<222> LOCATION: (1)..(1728)

<400> SEQUENCE: 9 atg ctg tgc tgc atg cga aga acc aaa cag gtt gaa aag aat gat gag      48
Met Leu Cys Cys Met Arg Arg Thr Lys Gln Val Glu Lys Asn Asp Glu
1               5                   10                  15 gac caa aag atc cac cgg ccg gtc gcc acc atg gtg agc aag ggc gag      96
Asp Gln Lys Ile His Arg Pro Val Ala Thr Met Val Ser Lys Gly Glu
            20                  25                  30 gag ctg ttc acc ggg gtg gtg ccc atc ctg gtc gag ctg gac ggc gac     144
Glu Leu Phe Thr Gly Val Val Pro Ile Leu Val Glu Leu Asp Gly Asp
        35                  40                  45 gta aac ggc cac aag ttc agc gtg tcc ggc gag ggc gag ggc gat gcc     192
Val Asn Gly His Lys Phe Ser Val Ser Gly Glu Gly Glu Gly Asp Ala
    50                  55                  60 acc tac ggc aag ctg acc ctg aag ttc atc tgc acc acc ggc aag ctg     240
Thr Tyr Gly Lys Leu Thr Leu Lys Phe Ile Cys Thr Thr Gly Lys Leu
65                  70                  75                  80 ccc gtg ccc tgg ccc acc ctc gtg acc acc ctg acc tgg ggc gtg cag     288
```

```
                Pro Val Pro Trp Pro Thr Leu Val Thr Thr Leu Thr Trp Gly Val Gln
                                85                  90                  95 tgc ttc agc cgc tac ccc gac cac atg aag cag cac gac ttc ttc aag          336
Cys Phe Ser Arg Tyr Pro Asp His Met Lys Gln His Asp Phe Phe Lys
                100                 105                 110 tcc gcc atg ccc gaa ggc tac gtc cag gag cgc acc atc ttc ttc aag          384
Ser Ala Met Pro Glu Gly Tyr Val Gln Glu Arg Thr Ile Phe Phe Lys
            115                 120                 125 gac gac ggc aac tac aag acc cgc gcc gag gtg aag ttc gag ggc gac          432
Asp Asp Gly Asn Tyr Lys Thr Arg Ala Glu Val Lys Phe Glu Gly Asp
        130                 135                 140 acc ctg gtg aac cgc atc gag ctg aag ggc atc gac ttc aag gag gac          480
Thr Leu Val Asn Arg Ile Glu Leu Lys Gly Ile Asp Phe Lys Glu Asp
145                 150                 155                 160 ggc aac atc ctg ggg cac aag ctg gag tac aac tac atc agc cac aac          528
Gly Asn Ile Leu Gly His Lys Leu Glu Tyr Asn Tyr Ile Ser His Asn
                165                 170                 175 gtc tat atc acc gcc gac aag cag aag aac ggc atc aag gcc aac ttc          576
Val Tyr Ile Thr Ala Asp Lys Gln Lys Asn Gly Ile Lys Ala Asn Phe
                180                 185                 190 aag atc cgc cac aac atc gag gac ggc agc gtg cag ctc gcc gac cac          624
Lys Ile Arg His Asn Ile Glu Asp Gly Ser Val Gln Leu Ala Asp His
            195                 200                 205 tac cag cag aac acc ccc atc ggc gac ggc ccc gtg ctg ctg ccc gac          672
Tyr Gln Gln Asn Thr Pro Ile Gly Asp Gly Pro Val Leu Leu Pro Asp
        210                 215                 220 aac cac tac ctg agc acc cag tcc gcc ctg agc aaa gac ccc aac gag          720
Asn His Tyr Leu Ser Thr Gln Ser Ala Leu Ser Lys Asp Pro Asn Glu
225                 230                 235                 240 aag cgc gat cac atg gtc ctg ctg gag ttc gtg acc gcc gcc ggg atc          768
Lys Arg Asp His Met Val Leu Leu Glu Phe Val Thr Ala Ala Gly Ile
                245                 250                 255 act ctc ggc atg gac gag ctg tac aag ctc gag att cca gaa gga gat          816
Thr Leu Gly Met Asp Glu Leu Tyr Lys Leu Glu Ile Pro Glu Gly Asp
                260                 265                 270 gaa gaa ggc aac atg gaa ctc agg cag aag ttt gag aaa gcc aag cta          864
Glu Glu Gly Asn Met Glu Leu Arg Gln Lys Phe Glu Lys Ala Lys Leu
            275                 280                 285 ggt cct gtt ggt aac aaa gtc atc agc cct tca gaa gac aga aag caa          912
Gly Pro Val Gly Asn Lys Val Ile Ser Pro Ser Glu Asp Arg Lys Gln
        290                 295                 300 cca tcc aac aac ctg gac aga gtg aaa ctc aca ctc gag ggc tcc ggt          960
Pro Ser Asn Asn Leu Asp Arg Val Lys Leu Thr Leu Glu Gly Ser Gly
305                 310                 315                 320 tct ggt cag cag gaa gtc tac ggt atg atg cct cgt gat ggt tct ggt         1008
Ser Gly Gln Gln Glu Val Tyr Gly Met Met Pro Arg Asp Gly Ser Gly
                325                 330                 335 atg gtg agc aag ggc gag gag ctg ttc acc ggg gtg gtg ccc atc ctg         1056
Met Val Ser Lys Gly Glu Glu Leu Phe Thr Gly Val Val Pro Ile Leu
                340                 345                 350 gtc gag ctg gac ggc gac gta aac ggc cac aag ttc agc gtg tcc ggc         1104
Val Glu Leu Asp Gly Asp Val Asn Gly His Lys Phe Ser Val Ser Gly
            355                 360                 365 gag ggc gag ggc gat gcc acc tac ggc aag ctg acc ctg aag ttc atc         1152
Glu Gly Glu Gly Asp Ala Thr Tyr Gly Lys Leu Thr Leu Lys Phe Ile
        370                 375                 380 tgc acc acc ggc aag ctg ccc gtg ccc tgg ccc acc ctc gtg acc acc         1200
Cys Thr Thr Gly Lys Leu Pro Val Pro Trp Pro Thr Leu Val Thr Thr
385                 390                 395                 400
```

```
ttc ggc tac ggc ctg cag tgc ttc gcc cgc tac ccc gac cac atg aag      1248
Phe Gly Tyr Gly Leu Gln Cys Phe Ala Arg Tyr Pro Asp His Met Lys
                405                 410                 415 cag cac gac ttc ttc aag tcc gcc atg ccc gaa ggc tac gtc cag gag      1296
Gln His Asp Phe Phe Lys Ser Ala Met Pro Glu Gly Tyr Val Gln Glu
            420                 425                 430 cgc acc atc ttc ttc aag gac gac ggc aac tac aag acc cgc gcc gag      1344
Arg Thr Ile Phe Phe Lys Asp Asp Gly Asn Tyr Lys Thr Arg Ala Glu
        435                 440                 445 gtg aag ttc gag ggc gac acc ctg gtg aac cgc atc gag ctg aag ggc      1392
Val Lys Phe Glu Gly Asp Thr Leu Val Asn Arg Ile Glu Leu Lys Gly
    450                 455                 460 atc gac ttc aag gag gac ggc aac atc ctg ggg cac aag ctg gag tac      1440
Ile Asp Phe Lys Glu Asp Gly Asn Ile Leu Gly His Lys Leu Glu Tyr
465                 470                 475                 480 aac tac aac agc cac aac gtc tat atc atg gcc gac aag cag aag aac      1488
Asn Tyr Asn Ser His Asn Val Tyr Ile Met Ala Asp Lys Gln Lys Asn
                485                 490                 495 ggc atc aag gtg aac ttc aag atc cgc cac aac atc gag gac ggc agc      1536
Gly Ile Lys Val Asn Phe Lys Ile Arg His Asn Ile Glu Asp Gly Ser
            500                 505                 510 gtg cag ctc gcc gac cac tac cag cag aac acc ccc atc ggc gac ggc      1584
Val Gln Leu Ala Asp His Tyr Gln Gln Asn Thr Pro Ile Gly Asp Gly
        515                 520                 525 ccc gtg ctg ctg ccc gac aac cac tac ctg agc tac cag tcc gcc ctg      1632
Pro Val Leu Leu Pro Asp Asn His Tyr Leu Ser Tyr Gln Ser Ala Leu
    530                 535                 540 agc aaa gac ccc aac gag aag cgc gat cac atg gtc ctg ctg gag ttc      1680
Ser Lys Asp Pro Asn Glu Lys Arg Asp His Met Val Leu Leu Glu Phe
545                 550                 555                 560 gtg acc gcc gcc ggg atc act ctc ggc atg gac gag ctg tac aag taa      1728
Val Thr Ala Ala Gly Ile Thr Leu Gly Met Asp Glu Leu Tyr Lys
                565                 570                 575

<210> SEQ ID NO 10
<211> LENGTH: 575
<212> TYPE: PRT
<213> ORGANISM: Artificial
<220> FEATURE:
<223> OTHER INFORMATION: F alpha

<400> SEQUENCE: 10

Met Leu Cys Cys Met Arg Arg Thr Lys Gln Val Glu Lys Asn Asp Glu
1               5                   10                  15

Asp Gln Lys Ile His Arg Pro Val Ala Thr Met Val Ser Lys Gly Glu
                20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
        50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Trp Gly Val Gln
                85                  90                  95

Cys Phe Ser Arg Tyr Pro Asp His Met Lys Gln His Asp Phe Phe Lys
            100                 105                 110

Ser Ala Met Pro Glu Gly Tyr Val Gln Glu Arg Thr Ile Phe Phe Lys
        115                 120                 125

Asp Asp Gly Asn Tyr Lys Thr Arg Ala Glu Val Lys Phe Glu Gly Asp
```

-continued

```
            130                 135                 140
Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Ile Ser His Asn
                165                 170                 175

Val Tyr Ile Thr Ala Asp Lys Gln Lys Asn Gly Ile Lys Ala Asn Phe
                180                 185                 190

Lys Ile Arg His Asn Ile Glu Asp Gly Ser Val Gln Leu Ala Asp His
                195                 200                 205

Tyr Gln Gln Asn Thr Pro Ile Gly Asp Gly Pro Val Leu Leu Pro Asp
210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys Leu Glu Ile Pro Glu Gly Asp
                260                 265                 270

Glu Glu Gly Asn Met Glu Leu Arg Gln Lys Phe Glu Lys Ala Lys Leu
                275                 280                 285

Gly Pro Val Gly Asn Lys Val Ile Ser Pro Ser Glu Asp Arg Lys Gln
290                 295                 300

Pro Ser Asn Asn Leu Asp Arg Val Lys Leu Thr Leu Glu Gly Ser Gly
305                 310                 315                 320

Ser Gly Gln Gln Glu Val Tyr Gly Met Met Pro Arg Asp Gly Ser Gly
                325                 330                 335

Met Val Ser Lys Gly Glu Glu Leu Phe Thr Gly Val Val Pro Ile Leu
                340                 345                 350

Val Glu Leu Asp Gly Asp Val Asn Gly His Lys Phe Ser Val Ser Gly
                355                 360                 365

Glu Gly Glu Gly Asp Ala Thr Tyr Gly Lys Leu Thr Leu Lys Phe Ile
                370                 375                 380

Cys Thr Thr Gly Lys Leu Pro Val Pro Trp Pro Thr Leu Val Thr Thr
385                 390                 395                 400

Phe Gly Tyr Gly Leu Gln Cys Phe Ala Arg Tyr Pro Asp His Met Lys
                405                 410                 415

Gln His Asp Phe Phe Lys Ser Ala Met Pro Glu Gly Tyr Val Gln Glu
                420                 425                 430

Arg Thr Ile Phe Phe Lys Asp Asp Gly Asn Tyr Lys Thr Arg Ala Glu
                435                 440                 445

Val Lys Phe Glu Gly Asp Thr Leu Val Asn Arg Ile Glu Leu Lys Gly
                450                 455                 460

Ile Asp Phe Lys Glu Asp Gly Asn Ile Leu Gly His Lys Leu Glu Tyr
465                 470                 475                 480

Asn Tyr Asn Ser His Asn Val Tyr Ile Met Ala Asp Lys Gln Lys Asn
                485                 490                 495

Gly Ile Lys Val Asn Phe Lys Ile Arg His Asn Ile Glu Asp Gly Ser
                500                 505                 510

Val Gln Leu Ala Asp His Tyr Gln Gln Asn Thr Pro Ile Gly Asp Gly
                515                 520                 525

Pro Val Leu Leu Pro Asp Asn His Tyr Leu Ser Tyr Gln Ser Ala Leu
                530                 535                 540

Ser Lys Asp Pro Asn Glu Lys Arg Asp His Met Val Leu Leu Glu Phe
545                 550                 555                 560
```

```
                Val Thr Ala Ala Gly Ile Thr Leu Gly Met Asp Glu Leu Tyr Lys
                            565                 570                 575

<210> SEQ ID NO 11
<211> LENGTH: 1737
<212> TYPE: DNA
<213> ORGANISM: Artificial
<220> FEATURE:
<223> OTHER INFORMATION: F beta
<220> FEATURE:
<221> NAME/KEY: CDS
<222> LOCATION: (1)..(1737)

<400> SEQUENCE: 11 atg ctg tgc tgc atg cga aga acc aaa cag gtt gaa aag aat gat gag        48
Met Leu Cys Cys Met Arg Arg Thr Lys Gln Val Glu Lys Asn Asp Glu
1               5                  10                  15 gac caa aag atc cac cgg ccg gtc gcc acc atg gtg agc aag ggc gag        96
Asp Gln Lys Ile His Arg Pro Val Ala Thr Met Val Ser Lys Gly Glu
            20                  25                  30 gag ctg ttc acc ggg gtg gtg ccc atc ctg gtc gag ctg gac ggc gac       144
Glu Leu Phe Thr Gly Val Val Pro Ile Leu Val Glu Leu Asp Gly Asp
        35                  40                  45 gta aac ggc cac aag ttc agc gtg tcc ggc gag ggc gag ggc gat gcc       192
Val Asn Gly His Lys Phe Ser Val Ser Gly Glu Gly Glu Gly Asp Ala
    50                  55                  60 acc tac ggc aag ctg acc ctg aag ttc atc tgc acc acc ggc aag ctg       240
Thr Tyr Gly Lys Leu Thr Leu Lys Phe Ile Cys Thr Thr Gly Lys Leu
65                  70                  75                  80 ccc gtg ccc tgg ccc acc ctc gtg acc acc ctg acc tgg ggc gtg cag       288
Pro Val Pro Trp Pro Thr Leu Val Thr Thr Leu Thr Trp Gly Val Gln
                85                  90                  95 tgc ttc agc cgc tac ccc gac cac atg aag cag cac gac ttc ttc aag       336
Cys Phe Ser Arg Tyr Pro Asp His Met Lys Gln His Asp Phe Phe Lys
            100                 105                 110 tcc gcc atg ccc gaa ggc tac gtc cag gag cgc acc atc ttc ttc aag       384
Ser Ala Met Pro Glu Gly Tyr Val Gln Glu Arg Thr Ile Phe Phe Lys
        115                 120                 125 gac gac ggc aac tac aag acc cgc gcc gag gtg aag ttc gag ggc gac       432
Asp Asp Gly Asn Tyr Lys Thr Arg Ala Glu Val Lys Phe Glu Gly Asp
    130                 135                 140 acc ctg gtg aac cgc atc gag ctg aag ggc atc gac ttc aag gag gac       480
Thr Leu Val Asn Arg Ile Glu Leu Lys Gly Ile Asp Phe Lys Glu Asp
145                 150                 155                 160 ggc aac atc ctg ggg cac aag ctg gag tac aac tac atc agc cac aac       528
Gly Asn Ile Leu Gly His Lys Leu Glu Tyr Asn Tyr Ile Ser His Asn
                165                 170                 175 gtc tat atc acc gcc gac aag cag aag aac ggc atc aag gcc aac ttc       576
Val Tyr Ile Thr Ala Asp Lys Gln Lys Asn Gly Ile Lys Ala Asn Phe
            180                 185                 190 aag atc cgc cac aac atc gag gac ggc agc gtg cag ctc gcc gac cac       624
Lys Ile Arg His Asn Ile Glu Asp Gly Ser Val Gln Leu Ala Asp His
        195                 200                 205 tac cag cag aac acc ccc atc ggc gac ggc ccc gtg ctg ctg ccc gac       672
Tyr Gln Gln Asn Thr Pro Ile Gly Asp Gly Pro Val Leu Leu Pro Asp
    210                 215                 220 aac cac tac ctg agc acc cag tcc gcc ctg agc aaa gac ccc aac gag       720
Asn His Tyr Leu Ser Thr Gln Ser Ala Leu Ser Lys Asp Pro Asn Glu
225                 230                 235                 240 aag cgc gat cac atg gtc ctg ctg gag ttc gtg acc gcc gcc ggg atc       768
Lys Arg Asp His Met Val Leu Leu Glu Phe Val Thr Ala Ala Gly Ile
```

```
                    245                 250                 255
act ctc ggc atg gac gag ctg tac aag ctc gag gtg ccg ccc gaa gga    816
Thr Leu Gly Met Asp Glu Leu Tyr Lys Leu Glu Val Pro Pro Glu Gly
            260                 265                 270 agc gag ggc aat gaa gag ctg cgg cag aag ttt gag aga gcc aag att    864
Ser Glu Gly Asn Glu Glu Leu Arg Gln Lys Phe Glu Arg Ala Lys Ile
        275                 280                 285 ggc caa ggt acc aag gct cca gaa gaa aag aca gct aac act atc tcc    912
Gly Gln Gly Thr Lys Ala Pro Glu Glu Lys Thr Ala Asn Thr Ile Ser
    290                 295                 300 aaa ttt gac aac aat ggc aac agg gac cgg atg aaa ctg acc ctc gag    960
Lys Phe Asp Asn Asn Gly Asn Arg Asp Arg Met Lys Leu Thr Leu Glu
305                 310                 315                 320 ggc tcc ggt tct ggt cag cag gaa gtc tac ggt atg atg cct cgt gat   1008
Gly Ser Gly Ser Gly Gln Gln Glu Val Tyr Gly Met Met Pro Arg Asp
                325                 330                 335 ggt tct ggt atg gtg agc aag ggc gag gag ctg ttc acc ggg gtg gtg   1056
Gly Ser Gly Met Val Ser Lys Gly Glu Glu Leu Phe Thr Gly Val Val
            340                 345                 350 ccc atc ctg gtc gag ctg gac ggc gac gta aac ggc cac aag ttc agc   1104
Pro Ile Leu Val Glu Leu Asp Gly Asp Val Asn Gly His Lys Phe Ser
        355                 360                 365 gtg tcc ggc gag ggc gag ggc gat gcc acc tac ggc aag ctg acc ctg   1152
Val Ser Gly Glu Gly Glu Gly Asp Ala Thr Tyr Gly Lys Leu Thr Leu
    370                 375                 380 aag ttc atc tgc acc acc ggc aag ctg ccc gtg ccc tgg ccc acc ctc   1200
Lys Phe Ile Cys Thr Thr Gly Lys Leu Pro Val Pro Trp Pro Thr Leu
385                 390                 395                 400 gtg acc acc ttc ggc tac ggc ctg cag tgc ttc gcc cgc tac ccc gac   1248
Val Thr Thr Phe Gly Tyr Gly Leu Gln Cys Phe Ala Arg Tyr Pro Asp
                405                 410                 415 cac atg aag cag cac gac ttc ttc aag tcc gcc atg ccc gaa ggc tac   1296
His Met Lys Gln His Asp Phe Phe Lys Ser Ala Met Pro Glu Gly Tyr
            420                 425                 430 gtc cag gag cgc acc atc ttc ttc aag gac gac ggc aac tac aag acc   1344
Val Gln Glu Arg Thr Ile Phe Phe Lys Asp Asp Gly Asn Tyr Lys Thr
        435                 440                 445 cgc gcc gag gtg aag ttc gag ggc gac acc ctg gtg aac cgc atc gag   1392
Arg Ala Glu Val Lys Phe Glu Gly Asp Thr Leu Val Asn Arg Ile Glu
    450                 455                 460 ctg aag ggc atc gac ttc aag gag gac ggc aac atc ctg ggg cac aag   1440
Leu Lys Gly Ile Asp Phe Lys Glu Asp Gly Asn Ile Leu Gly His Lys
465                 470                 475                 480 ctg gag tac aac tac aac agc cac aac gtc tat atc atg gcc gac aag   1488
Leu Glu Tyr Asn Tyr Asn Ser His Asn Val Tyr Ile Met Ala Asp Lys
                485                 490                 495 cag aag aac ggc atc aag gtg aac ttc aag atc cgc cac aac atc gag   1536
Gln Lys Asn Gly Ile Lys Val Asn Phe Lys Ile Arg His Asn Ile Glu
            500                 505                 510 gac ggc agc gtg cag ctc gcc gac cac tac cag cag aac acc ccc atc   1584
Asp Gly Ser Val Gln Leu Ala Asp His Tyr Gln Gln Asn Thr Pro Ile
        515                 520                 525 ggc gac ggc ccc gtg ctg ctg ccc gac aac cac tac ctg agc tac cag   1632
Gly Asp Gly Pro Val Leu Leu Pro Asp Asn His Tyr Leu Ser Tyr Gln
    530                 535                 540 tcc gcc ctg agc aaa gac ccc aac gag aag cgc gat cac atg gtc ctg   1680
Ser Ala Leu Ser Lys Asp Pro Asn Glu Lys Arg Asp His Met Val Leu
545                 550                 555                 560 ctg gag ttc gtg acc gcc gcc ggg atc act ctc ggc atg gac gag ctg   1728
```

-continued

```
Leu Glu Phe Val Thr Ala Ala Gly Ile Thr Leu Gly Met Asp Glu Leu
                565                 570                 575 tac aag taa                                                         1737
Tyr Lys <210> SEQ ID NO 12
<211> LENGTH: 578
<212> TYPE: PRT
<213> ORGANISM: Artificial
<220> FEATURE:
<223> OTHER INFORMATION: F beta

<400> SEQUENCE: 12

Met Leu Cys Cys Met Arg Arg Thr Lys Gln Val Glu Lys Asn Asp Glu
1               5                   10                  15

Asp Gln Lys Ile His Arg Pro Val Ala Thr Met Val Ser Lys Gly Glu
                20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
        50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Trp Gly Val Gln
                85                  90                  95

Cys Phe Ser Arg Tyr Pro Asp His Met Lys Gln His Asp Phe Phe Lys
                100                 105                 110

Ser Ala Met Pro Glu Gly Tyr Val Gln Glu Arg Thr Ile Phe Phe Lys
            115                 120                 125

Asp Asp Gly Asn Tyr Lys Thr Arg Ala Glu Val Lys Phe Glu Gly Asp
        130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Ile Ser His Asn
                165                 170                 175

Val Tyr Ile Thr Ala Asp Lys Gln Lys Asn Gly Ile Lys Ala Asn Phe
                180                 185                 190

Lys Ile Arg His Asn Ile Glu Asp Gly Ser Val Gln Leu Ala Asp His
            195                 200                 205

Tyr Gln Gln Asn Thr Pro Ile Gly Asp Gly Pro Val Leu Leu Pro Asp
        210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys Leu Glu Val Pro Pro Glu Gly
                260                 265                 270

Ser Glu Gly Asn Glu Glu Leu Arg Gln Lys Phe Glu Arg Ala Lys Ile
            275                 280                 285

Gly Gln Gly Thr Lys Ala Pro Glu Glu Lys Thr Ala Asn Thr Ile Ser
        290                 295                 300

Lys Phe Asp Asn Asn Gly Asn Arg Asp Arg Met Lys Leu Thr Leu Glu
305                 310                 315                 320

Gly Ser Gly Ser Gly Gln Gln Glu Val Tyr Gly Met Met Pro Arg Asp
                325                 330                 335
```

-continued

```
Gly Ser Gly Met Val Ser Lys Gly Glu Glu Leu Phe Thr Gly Val Val
            340                 345                 350
Pro Ile Leu Val Glu Leu Asp Gly Asp Val Asn Gly His Lys Phe Ser
            355                 360                 365
Val Ser Gly Glu Gly Glu Gly Asp Ala Thr Tyr Gly Lys Leu Thr Leu
    370                 375                 380
Lys Phe Ile Cys Thr Thr Gly Lys Leu Pro Val Pro Trp Pro Thr Leu
385                 390                 395                 400
Val Thr Thr Phe Gly Tyr Gly Leu Gln Cys Phe Ala Arg Tyr Pro Asp
                405                 410                 415
His Met Lys Gln His Asp Phe Phe Lys Ser Ala Met Pro Glu Gly Tyr
            420                 425                 430
Val Gln Glu Arg Thr Ile Phe Phe Lys Asp Asp Gly Asn Tyr Lys Thr
            435                 440                 445
Arg Ala Glu Val Lys Phe Glu Gly Asp Thr Leu Val Asn Arg Ile Glu
    450                 455                 460
Leu Lys Gly Ile Asp Phe Lys Glu Asp Gly Asn Ile Leu Gly His Lys
465                 470                 475                 480
Leu Glu Tyr Asn Tyr Asn Ser His Asn Val Tyr Ile Met Ala Asp Lys
                485                 490                 495
Gln Lys Asn Gly Ile Lys Val Asn Phe Lys Ile Arg His Asn Ile Glu
            500                 505                 510
Asp Gly Ser Val Gln Leu Ala Asp His Tyr Gln Gln Asn Thr Pro Ile
            515                 520                 525
Gly Asp Gly Pro Val Leu Leu Pro Asp Asn His Tyr Leu Ser Tyr Gln
    530                 535                 540
Ser Ala Leu Ser Lys Asp Pro Asn Glu Lys Arg Asp His Met Val Leu
545                 550                 555                 560
Leu Glu Phe Val Thr Ala Ala Gly Ile Thr Leu Gly Met Asp Glu Leu
                565                 570                 575
Tyr Lys

<210> SEQ ID NO 13
<211> LENGTH: 10
<212> TYPE: PRT
<213> ORGANISM: Artificial
<220> FEATURE:
<223> OTHER INFORMATION: GAP-43 palmitoylation signal (10 a.a.)

<400> SEQUENCE: 13

Met Leu Cys Cys Met Arg Arg Thr Lys Gln
1               5                   10

<210> SEQ ID NO 14
<211> LENGTH: 14
<212> TYPE: PRT
<213> ORGANISM: Artificial
<220> FEATURE:
<223> OTHER INFORMATION: c-src myristoylation signal

<400> SEQUENCE: 14

Met Gly Ser Ser Lys Ser Lys Pro Lys Asp Pro Ser Gln Arg
1               5                   10
```